US012599364B2

(12) United States Patent
Tepper

(10) Patent No.: US 12,599,364 B2
(45) Date of Patent: Apr. 14, 2026

(54) ULTRASOUND SIMULATION SYSTEM

(71) Applicant: Simhawk Ltd., Petah Tikva (IL)

(72) Inventor: Rafael Ron Tepper, Petah Tikva (IL)

(73) Assignee: Simhawk Ltd., Petah Tikva (IL)

( * ) Notice: Subject to any disclaimer, the term of this patent is extended or adjusted under 35 U.S.C. 154(b) by 364 days.

(21) Appl. No.: 18/039,524

(22) PCT Filed: Oct. 11, 2021

(86) PCT No.: PCT/IL2021/051214
§ 371 (c)(1),
(2) Date: May 31, 2023

(87) PCT Pub. No.: WO2022/118305
PCT Pub. Date: Jun. 9, 2022

(65) Prior Publication Data
US 2024/0008845 A1     Jan. 11, 2024

Related U.S. Application Data

(60) Provisional application No. 63/119,664, filed on Dec. 1, 2020.

(51) Int. Cl.
*A61B 8/00* (2006.01)
*A61B 90/00* (2016.01)

(52) U.S. Cl.
CPC .......... *A61B 8/4245* (2013.01); *A61B 8/4483* (2013.01); *A61B 8/461* (2013.01);
(Continued)

(58) Field of Classification Search
CPC .................................................. A61B 8/4245
See application file for complete search history.

(56) References Cited

U.S. PATENT DOCUMENTS

| | | | |
|---|---|---|---|
| 5,938,607 A | 8/1999 | Jago et al. | |
| 7,782,319 B2 | 8/2010 | Ghosh et al. | |

(Continued)

FOREIGN PATENT DOCUMENTS

| | | |
|---|---|---|
| WO | WO 2007/100263 | 9/2007 |
| WO | WO 2022/118305 | 6/2022 |

OTHER PUBLICATIONS

International Preliminary Report on Patentability Jun. 15, 2023 From the International Bureau of WIPO Re. Application No. PCT IL2021/051214. (13 Pages).

(Continued)

*Primary Examiner* — Jerry T Jean Baptiste

(57) ABSTRACT

Aspects of some embodiments of the invention relate to systems and methods for simulating an ultrasound, comprising a camera, a physical tridimensional reference element attached to an ultrasound transducer of an ultrasound device and a processing module comprising instructions to perform the following while performing an ultrasound examination or after performing the ultrasound examination and spatial location of the documented information: digitally imaging a physical tridimensional reference element, determining from said imaging a second spatial data of said physical tridimensional reference element relative to a virtual location-identifying orientation; displaying said ultrasound data when said second spatial data is the same as said first spatial data and said orientation of a patient is the same as said virtual location-identifying orientation.

24 Claims, 22 Drawing Sheets

(52) U.S. Cl.
     CPC ............ *A61B 8/5238* (2013.01); *A61B 90/36*
                    (2016.02); *A61B 2090/365* (2016.02)

(56)                 References Cited

U.S. PATENT DOCUMENTS

|  |  |  |  |
|---|---|---|---|
| 8,116,549 B2 | 2/2012 | Warmath |  |
| 2001/0033281 A1 | 10/2001 | Yoshida |  |
| 2004/0106869 A1 | 6/2004 | Tepper |  |
| 2010/0179428 A1 | 7/2010 | Pedersen et al. |  |
| 2011/0060579 A1 | 3/2011 | Butsev et al. |  |
| 2011/0190629 A1 | 8/2011 | Guenther et al. |  |
| 2013/0137988 A1 | 5/2013 | Bregman-Amitai et al. |  |
| 2014/0004488 A1 | 1/2014 | Tepper et al. |  |
| 2014/0051922 A1 | 2/2014 | Gruther et al. |  |
| 2014/0163376 A1* | 6/2014 | Caluser ................. | G16H 30/20 |
|  |  |  | 600/443 |
| 2015/0056591 A1 | 2/2015 | Tepper et al. |  |
| 2015/0140538 A1 | 5/2015 | Savitsky |  |
| 2016/0270656 A1* | 9/2016 | Samec ................... | A61B 5/398 |
| 2016/0284240 A1 | 9/2016 | Liang |  |
| 2017/0079723 A1 | 3/2017 | Fleig et al. |  |
| 2017/0245940 A1 | 8/2017 | Piron et al. |  |
| 2018/0068590 A1 | 3/2018 | Mattausch et al. |  |
| 2019/0197920 A1 | 6/2019 | Abella et al. |  |

OTHER PUBLICATIONS

International Search Report and the Written Opinion Dated Mar. 2, 2022 From the International Searching Authority Re. Application No. PCT/IL2021/051214. (17 Pages).

Invitation to Pay Additional Fees Dated Dec. 14, 2021 From the International Searching Authority Re. Application No. PCT/IL2021/051214. (2 Pages).

Aiger et al. "Real-Time Ultrasound Imaging Simulation", Real-Time Imaging, 4(4):263-274, Aug. 1998.

Alhamzi et al. "3D Object Recognition Based on Image Features: A Survey", International Journal of Computer and Information Technology, 3(3): 651-660, May 2014.

Clark et al. "Quantitating Skill Acquisition With Optical Ultrasound Simulation", AJUM, Australian Journal of Ultrasound in Medicine, 23(3): 183-193, Published Online Aug. 2, 2020.

Gronnebaek Tolsgaard "Assessment and Learning of Ultrasound Skills in Obstetrics & Gynecology", Danish Medical Journal, 65(2): B5445-1-B5445-25, Feb. 2018.

Gunabushanam et al. "Accessible Personal Ultrasound Training Simulator", Journal of Ultrasound Medicine, 38(6): 1425-1432, Published Online Sep. 12, 2018.

Ostergaard et al. "Simulator Training Improves Ultrasound Scanning Performance on Patients: A Randomized Controlled Trial", European Radiology, 29(6): 3210-3218, Published Online Jan. 7, 2019.

Penev et al. "Marker-Based Method for 3D Object Recognition and Localization", Proceedings of the SPIE, Visiual Information Processing XII, AeroSense 2003, Orlando, Florida, USA, Aug. 8, 2003, 5108: 346-355, Aug. 8, 2003.

Schallware "Schallware Ultrasound Simulator: Internal Medicine, Obstetrics and Gynecology, Cardiology TTE, TEE, Urology, Pediatrics, Premature Births", Schallware GmbH, Product Sheet, p. 1-55, 2018/2019.

Tsai et al. "Creation and Validation of A Simulator for Neonatal Brain Ultrasonography: A Pilot Study", Academic Radiology, 24(1): 76-83, Jan. 2017.

Wiedemann et al. "Recognition and Tracking of 3D Objects", Proceedings of the 30th DAGM Symposium on Pattern Recognition, Munich, Germany, Jun. 10-13, 2008, 30: 132-141, Jun. 10, 2008.

Xu et al. "Simulating Transvertebral Ultrasound Propagation with a Multi-Layered Ray Acoustics Model", Physics in Medicine & Biology, 63(14): 1-22, Jul. 17, 2018.

Supplementary European Search Report and the European Search Opinion Dated Sep. 20, 2024 From the European Patent Office Re. Application No. 21900215.1. (7 Pages).

\* cited by examiner

108

100

106     104

Software
102

Identifying at least one marker on the surface of the reference element 112 — 314

Generating virtual square behind marker on reference element — 316

Virtually generating two lines connecting center mass/center of square with angles of square, thereby generatin a triangle — 318

Utilizing triangle to correlate between ultrasound image with postion of reference element — 320

302

112

304

302

112

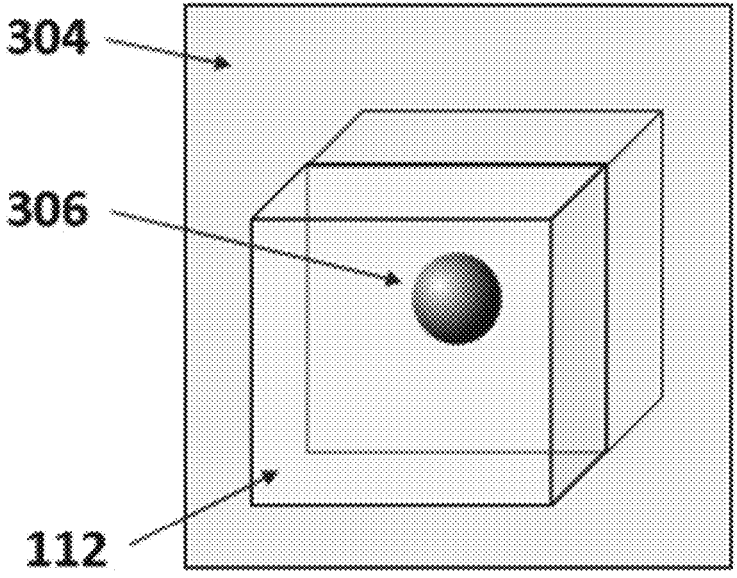
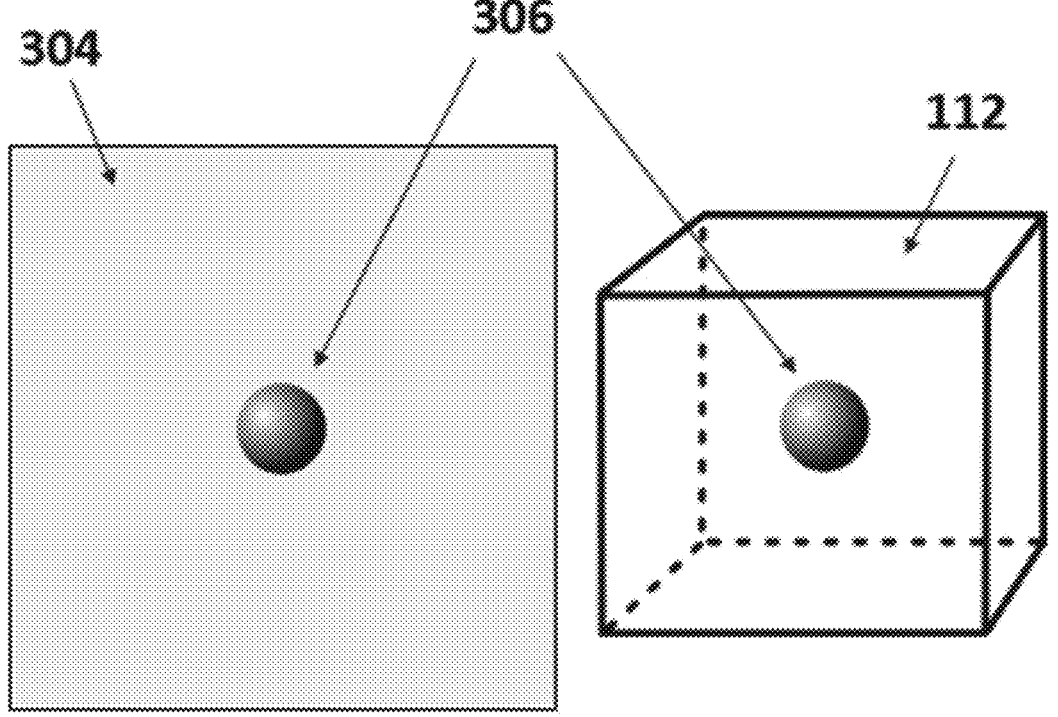
Figure 3e

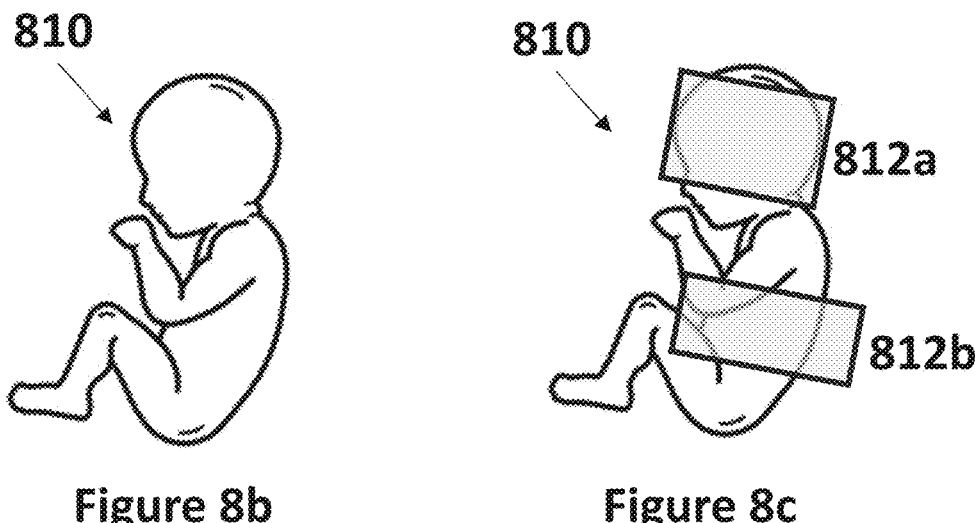
Figure 8a            808
Figure 8b            Figure 8c

110     112     906

ULTRASOUND SIMULATION SYSTEM

RELATED APPLICATION/S

This application is a National Phase of PCT Patent Application No. PCT/IL2021/051214 having International filing date of Oct. 11, 2021, which claims the benefit of priority under 35 USC § 119 (e)_of U.S. Provisional Patent Application No. 63/119,664 filed on Dec. 1, 2020. The contents of the above applications are all incorporated by reference as if fully set forth herein in their entirety.

FIELD AND BACKGROUND

The present invention, in some embodiments thereof, relates to a simulation system and, more particularly, but not exclusively, to an ultrasound simulation system. Additional background art includes U.S. Patent Application No. US20140004488A1 discloses a system for training practitioners in use of an ultrasound system including a unit for managing workflow of an ultrasound training session, a user interface for providing ultrasound training session instructions to a practitioner operating an ultrasound machine and for receiving input from a trainee, a unit for communication with the ultrasound machine, for collecting one or more ultrasound images produced during the training session from the ultrasound machine, a unit for image processing the ultrasound images, and a unit for assessing quality of the ultrasound images. A method for monitoring practitioner proficiency in use of an ultrasound system including providing the practitioner with an ultrasound task definition, collecting one or more ultrasound images produced by the practitioner during performance of the ultrasound task from an ultrasound machine, image processing the ultrasound images, and assessing quality of the ultrasound images. Related apparatus and methods are also described.

U.S. Pat. No. 7,782,319 discloses a method, apparatus, and article of manufacture that provide the ability to control a three-dimensional scene view. A three-dimensional (3D) scene having one or more three-dimensional objects is displayed. A 3D representation of a coordinate system of the scene is displayed. The 3D representation contains a current viewpoint, one or more faces, one or more edges, and one or more corners with each face, edge, and corner representing a corresponding viewpoint of the scene. The 3D representation is manipulated. A new current viewpoint of the 3D representation is displayed based on the manipulation. The scene is then reoriented corresponding to the new current viewpoint based on the manipulation of the 3D representation.

U.S. Patent Application No. US20040106869A1 discloses an apparatus for precision location of a tool such as a surgical tool within an obscured region such as an internal space of the human or animal body, the apparatus comprising: a planar scanning unit for scanning planes within said obscured region using an imaging scan, and a locator, associated with said tool and with said scanning unit, for determining a location of said tool, and for selecting a plane including said tool location. The apparatus allows the planar scan to follow the tool automatically and saves skill and effort on the part of the surgeon.

U.S. Patent Application No. US20130137988A1 discloses an augmented ultrasound examination system, that comprises: a) an ultrasound system suitable to generate images of a body portion; b) a first position sensor coupled to the ultrasound transducer of said ultrasound system; c) a second position sensor suitable to be coupled to a finger; and d) data processing apparatus suitable to receive position information from said first and from said that second position sensors and to generate therefrom information correlating on a screen the position of said second position sensor with the image generated by said ultrasound system.

U.S. Patent Application No. US20150056591A1 discloses methods and devices for simulating ultrasound procedures and for training ultrasound users. Additionally disclosed are methods and devices for simulating needle insertion procedures, such as amniocentesis procedures, and for training physicians to perform such needle insertion procedures.

SUMMARY

Following is a non-exclusive list including some examples of embodiments of the invention. The invention also includes embodiments which include fewer than all the features in an example and embodiments using features from multiple examples, also if not expressly listed below.

Example 1. A method for simulating an ultrasound, comprising:

a. providing an ultrasound library database of ultrasound data and corresponding first spatial data of a transducer during which said ultrasound data was acquired relative to an orientation of a target;

b. digitally imaging a physical tridimensional reference element;

c. determining from said imaging a second spatial data of said physical tridimensional reference element relative to a virtual location-identifying orientation;

d. displaying said ultrasound data when said second spatial data is the same as said first spatial data and said orientation of a patient is the same as said virtual location-identifying orientation.

Example 2. The method according to example 1, wherein said providing an ultrasound library database of a plurality of ultrasound data comprises providing one or more of ultrasound images, ultrasound videos and ultrasound volumes.

Example 3. The method according to example 1 or example 2, wherein said displaying said ultrasound data comprises displaying said ultrasound data according to a predetermined order.

Example 4. The method according to example 3, wherein said predetermined order is according to a quality of said ultrasound data.

Example 5. The method according to example 3, wherein said predetermined order is ultrasound video, ultrasound image and ultrasound volume.

Example 6. The method according to anyone of examples 1-5, wherein said displaying said ultrasound data comprises displaying a merged image from said one or more of ultrasound images, ultrasound videos and ultrasound volumes.

Example 7. The method according to anyone of examples 1-6, wherein said first and said second spatial data comprises one or more movements and directions selected from the group consisting of up, down, forward, backwards, right, left roll, yaw, pitch and any combination thereof.

Example 8. The method according to anyone of examples 1-7, wherein said virtual location-identifying orientation is a virtual orientation of one or more of a virtual patient and a virtual target.

Example 9. The method according to anyone of examples 1-8, wherein said physical tridimensional reference element comprises at least one reference markings.

Example 10. The method according to anyone of examples 1-9, wherein said determining said second spatial data of said tridimensional reference element comprises one or more of:

a. identifying said at least one reference markings;

b. identifying movements of said tridimensional reference element according to said identification; and c. correlating said identified movements with said virtual location-identifying orientation.

Example 11. An ultrasound simulation system, comprising:

a. a physical tridimensional reference element;

b. a software configured for identifying an image of said physical tridimensional reference element and requesting ultrasound data according to said image.

Example 11a. The ultrasound simulation system according to example 11, wherein said physical tridimensional reference element comprises a hexagonal prism form.

Example 12. The ultrasound simulation system according to example 11 or example 11a, wherein said physical tridimensional reference element comprises at least one reference markings.

Example 13. The ultrasound simulation system according to example 11, 11a or example 12, wherein said image is identified from data received from a camera.

Example 14. The ultrasound simulation system according to any one of examples 11-13, wherein said ultrasound data is one or more of ultrasound images, ultrasound videos and ultrasound volumes.

Example 15. The ultrasound simulation system according to any one of examples 11-14, wherein an ultrasound data provided due to said request is a selected algorithmic ultrasound data.

Example 16. The ultrasound simulation system according to example 15, wherein said one or more of ultrasound images, ultrasound videos and ultrasound volumes are cataloged in said ultrasound library using a spatial correlation between each other according to what is shown in them.

Example 17. The ultrasound simulation system according to anyone of examples 11-16, wherein said displaying said ultrasound data comprises displaying said ultrasound data according to a predetermined order.

Example 18. The ultrasound simulation system according to example 17, wherein said predetermined order is according to a quality of said ultrasound data.

Example 19. The ultrasound simulation system according to example 17, wherein said predetermined order is ultrasound video, ultrasound volume and ultrasound image.

Example 20. The ultrasound simulation system according to anyone of examples 11-19, wherein said displaying said ultrasound data comprises displaying a merged image from said one or more of ultrasound images, ultrasound videos and ultrasound volumes.

Example 21. The ultrasound simulation system according to anyone of examples 11-20, wherein said software is further configured for identifying spatial data of said physical tridimensional reference element comprising one or more movements selected from the group consisting of up, down, forward, backwards, right, left roll, yaw, pitch and any combination thereof.

Example 22. The ultrasound simulation system according to anyone of examples 11-21, wherein said identifying comprises identifying a virtual location-identifying orientation which is a virtual orientation of one or more of a virtual patient and a virtual target.

Example 23. The ultrasound simulation system according to anyone of examples 11-21, wherein said physical tridimensional reference element comprises at least one selected from the group consisting of a light, a vibration mechanism and a speaker.

Example 24. The ultrasound simulation system according to anyone of examples 11-23, wherein said identifying an image of said physical tridimensional reference element comprises one or more of:

a. identifying said at least one reference markings;

b. identifying movements of said tridimensional reference element according to said identification; and c. correlating said identified movements with said virtual location-identifying orientation.

Example 25. The ultrasound simulation system according to anyone of examples 11-24, wherein said camera is an integral part of an electronic device.

Example 26. The ultrasound simulation system according to anyone of examples 11-25, wherein said system records said identified movements of said tridimensional reference element.

Example 27. The ultrasound simulation system according to anyone of examples 11-26, wherein said system records all information related to a performed simulation by a user comprising one or more of type of case simulated, identified movements of said tridimensional reference element, time to finish simulation, time to reach the requested area and images chosen to keep during simulation.

Example 27a. The ultrasound simulation system according to anyone of examples 11-27, wherein said system further comprises an augmented reality (AR) activator for activating an augmented reality image to be shown to a user while using said ultrasound simulation system.

Example 27b. The ultrasound simulation system according to anyone of examples 11-27a, wherein said augmented reality image is displayed on one or more of a display, a display on top of a real world image capture by said camera, a smart electronic device and a display on a smart glasses.

Example 28. An ultrasound simulation system, comprising:

a. a camera;

b. a physical tridimensional reference element; and c. an ultrasound library database comprising ultrasound data and corresponding first spatial data of a transducer during which said ultrasound data was acquired relative to an orientation of a patient;

d. a display module;

e. a processing module comprising instructions to:

i. digitally imaging a physical tridimensional reference element;

ii. determining from said imaging a second spatial data of said physical tridimensional reference element relative to a virtual location-identifying orientation;

iii. displaying said ultrasound data when said second spatial data is the same as said first spatial data and said orientation of a patient is the same as said virtual location-identifying orientation.

Example 29. The ultrasound simulation system according to example 28, wherein said ultrasound library database comprises one or more of 2D ultrasound data, 3D ultrasound data and ultrasound video data.

Example 30. The ultrasound simulation system according to example 28 or example 29, wherein said ultrasound data comprises providing one or more of ultrasound images, ultrasound videos and ultrasound volumes.

Example 31. The ultrasound simulation system according to example 28, wherein said one or more of ultrasound images, ultrasound videos and ultrasound volumes are cataloged in said ultrasound library using a spatial correlation between each other according to what is shown in them.

Example 32. The ultrasound simulation system according to anyone of examples 28-32, wherein said displaying said ultrasound data comprises displaying said ultrasound data according to a predetermined order.

Example 33. The ultrasound simulation system according to example 32, wherein said predetermined order is according to a quality of said ultrasound data.

Example 34. The ultrasound simulation system according to example 32, wherein said predetermined order is ultrasound video, ultrasound volume and ultrasound image.

Example 35. The ultrasound simulation system according to anyone of examples 28-34, wherein said displaying said ultrasound data comprises displaying a merged image from said one or more of ultrasound images, ultrasound videos and ultrasound volumes.

Example 36. The ultrasound simulation system according to anyone of examples 28-35, wherein said first and said second spatial data comprises one or more movements selected from the group consisting of up, down, forward, backwards, right, left roll, yaw, pitch and any combination thereof.

Example 37. The ultrasound simulation system according to anyone of examples 28-36, wherein said virtual location-identifying orientation is a virtual orientation of one or more of a virtual patient and a virtual target.

Example 38. The ultrasound simulation system according to anyone of examples 28-37, wherein said physical tridimensional reference element comprises at least one reference marking.

Example 38a. The ultrasound simulation system according to anyone of examples 28-38, wherein said physical tridimensional reference element comprises a hexagonal prism form.

Example 39. The ultrasound simulation system according to anyone of examples 28-38a, wherein said determining said second spatial data of said tridimensional reference element comprises one or more of:

a. identifying said at least one reference marking;
b. identifying movements of said tridimensional reference element according to said identification; and
c. correlating said identified movements with said virtual location-identifying orientation.

Example 40. The ultrasound simulation system according to anyone of examples 28-39, wherein said camera is an integral part of said electronic device.

Example 41. The ultrasound simulation system according to anyone of examples 28-40, wherein said system records said identified movements of said tridimensional reference element.

Example 42. The ultrasound simulation system according to anyone of examples 28-41, wherein said system records all information related to a performed simulation by a user comprising one or more of type of case simulated, identified movements of said tridimensional reference element, time to finish simulation, time to reach the requested area and images chosen to keep during simulation.

Example 42a. The ultrasound simulation system according to anyone of examples 28-42, wherein said system further comprises an augmented reality (AR) activator for activating an augmented reality image to be shown to a user while using said ultrasound simulation system.

Example 42b. The ultrasound simulation system according to anyone of examples 28-42a, wherein said augmented reality image is displayed on one or more of a display, a display on top of a real world image capture by said camera, a smart electronic device and a display on a smart glasses.

Example 43. A system for collecting ultrasound data, comprising:

a. a camera;
b. a physical tridimensional reference element attached to an ultrasound transducer of an ultrasound device;
c. a processing module comprising instructions to perform the following while performing an ultrasound examination:
i. digitally imaging said physical tridimensional reference element;
ii. collecting from said imaging, spatial data information of said physical tridimensional reference element relative to a location-identifying orientation;
iii. assigning said collected spatial data information to images collected by said ultrasound device at the same time during said ultrasound examination.

Example 44. The system according to example 43, further comprising an ultrasound library database where said ultrasound data is stored.

Example 45. The system according to example 43, wherein said location-identifying orientation is one or more of a virtual location, a real location, and a target.

Example 46. An automated system for collecting ultrasound data on a subject, comprising:

a. an ultrasound device comprising an ultrasound transducer configured to perform 2D ultrasound scans;
b. an object comprising one or more visual reference elements to be used as reference markers for a 3D tracking software; said object attached to said an ultrasound transducer;
c. a robotic arm comprising an attachment for reversibly attach said ultrasound transducer to said robotic arm;
d. a camera having optical field of view of said object, said transducer and said object;
e. a control system which controls said robotic arm, said ultrasound device and said camera.

Example 47. The system according to example 46, wherein said control system comprises a processor comprising instructions to:

a. instructing said robotic arm to perform a movement along a path;
b. activating said ultrasound device while said robotic arm is performing said movement;
c. activating said camera while said robotic arm is performing said movement;
d. digitally imaging said physical tridimensional reference element by means of said camera;
e. collecting from said imaging, spatial data information of said physical tridimensional reference element relative to a location-identifying orientation;
f. assigning said collected spatial data information to images collected by said ultrasound device at the same time during said ultrasound activation.

Example 48. The system according to example 46 or example 47, wherein said optical field of view of said camera comprises an optical field of view of a location where said transducer contacts a surface of said subject.

Example 49. The system according to any one of examples 46-48, further comprising an ultrasound library database where said ultrasound data is stored.

Example 50. The system according to any one of examples 46-49, wherein said location-identifying orientation is one or more of a virtual location, a real location, and a target.

Example 51. The system according to any one of examples 46-50, wherein said physical tridimensional reference element comprises a hexagonal prism form.

Example 52. The system according to any one of examples 46-51, wherein said system further comprises a 3D ultrasound transducer configured to perform 3D ultrasound scans.

Example 53. The system according to any one of examples 46-52, wherein said movement is a linear movement along a single axis.

Example 54. A method of automatically collecting ultrasound data on a subject utilizing an automated system, comprising:

a. instructing a robotic arm of said automated system to perform a movement along a path;

b. activating an ultrasound device comprising ultrasound transducer configured to perform 2D ultrasound scans while said robotic arm is performing said movement; said transducer comprising an attached object comprising one or more visual reference elements to be used as reference markers for a 3D tracking software;

c. activating a camera having optical field of view of said object, said transducer and said object while said robotic arm is performing said movement;

d. digitally imaging said object by means of said camera;

e. collecting from said imaging, spatial data information of said object relative to a location-identifying orientation;

f. assigning said collected spatial data information to images collected by said ultrasound device at the same time during said ultrasound activation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic representation of an exemplary system, according to some embodiments of the invention;

FIGS. 3c-h are schematic representations intended to help explain the exemplary method of translation between reference element and ultrasound image, according to some embodiments of the invention;

FIGS. 8a-c are schematic representations of an exemplary graphical unit interface (GUI) and displays thereof, according to some embodiments of the invention;

DESCRIPTION OF SPECIFIC EMBODIMENTS OF THE INVENTION

Figures 2A, 2B:
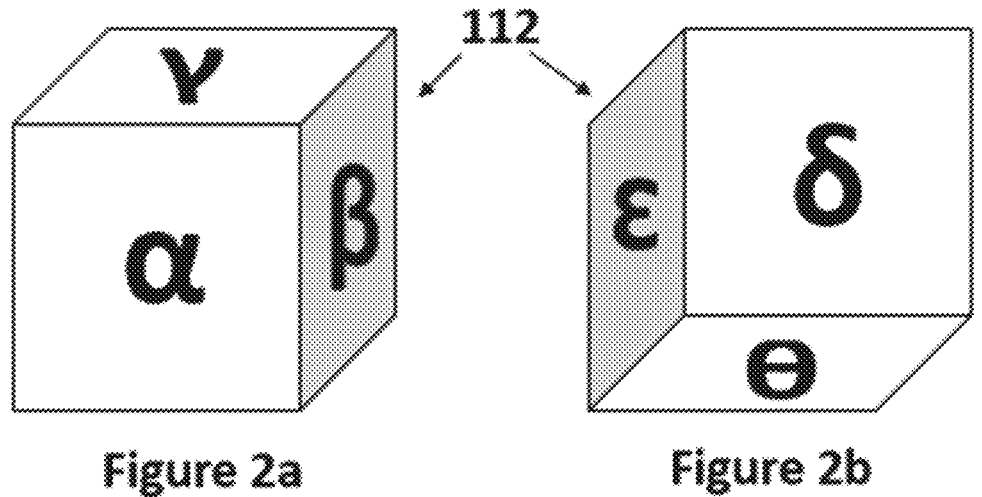
FIGS. 2a-d are schematic representations of exemplary reference elements, according to some embodiments of the invention.

The present invention, in some embodiments thereof, relates to an imaging simulation system and, more particularly, but not exclusively, to an ultrasound simulation system.

Overview

An aspect of some embodiments of the invention relates to an ultrasound simulation system that utilizes an object held by a user in the real world to choose what media to display to the user. In some embodiments, the system identifies markings on the object to identify its spatial movements. In some embodiments, the object comprises a hexagon form. In some embodiments, the ultrasound simulation system is used as an ultrasound training simulation system. In some embodiments, the system references those movements with stored virtual media, which are shown to a user. In some embodiments, the virtual media are one or more of ultrasound images and/or ultrasound videos and/or ultrasound volumes. In some embodiments, virtual media is enhanced by 3D spatial information of a transducer when the media was collected, meaning the movements performed by the transducer during the collection of the media are collected and incorporated to the information file of the media, therefore providing an enhanced media file comprising the movements of a transducer and the images showed by the transducer. In some embodiments, the system is configured to compare the spatial movements of the object in the real world with the saved 3D spatial information of the transducer when the media was collected, to choose which media to display. In some embodiments, the system comprises a plurality of media formats for a same location and the system is configured to show the best media, according to a predetermined order. For example, the system comprises a plurality of ultrasound images, ultrasound videos and ultrasound volumes of a neonatal heart, optionally from a plurality of different sources. In some embodiments, the system will display to the user the best quality media available. In some embodiments, an exemplary predetermined quality media order is ultrasound volume, ultrasound video and ultrasound images. In some embodiments, the system is configured to display more than one type media at the same time.

An aspect of some embodiments of the invention relate to an ultrasound simulation system configured to record the actions of users and to score them according to expected results and/or predetermined comparative data. In some embodiments, the system provides a task to the user and records all the actions performed by the user, including the spatial movements of a reference element, the images selected to be saved by the user, the time required from the user to achieve the task and more.

An aspect of some embodiments of the invention relates to an ultrasound collection system configured to collect ultrasound data and enhanced it with spatial information related to a transducer position when the ultrasound data was collected. In some embodiments, the ultrasound data is divided into the simplest of formats (for example a frame of an image) and uniquely indexed. In some embodiments, the unique indexing is used to easily recover and/or utilize the required ultrasound data. In some embodiments, the ultrasound collection system is a robotic scanner. In some embodiments, the robotic scanner performs linear 2D scans, which are then used to generate 3D volumes.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary System

Figure 1:
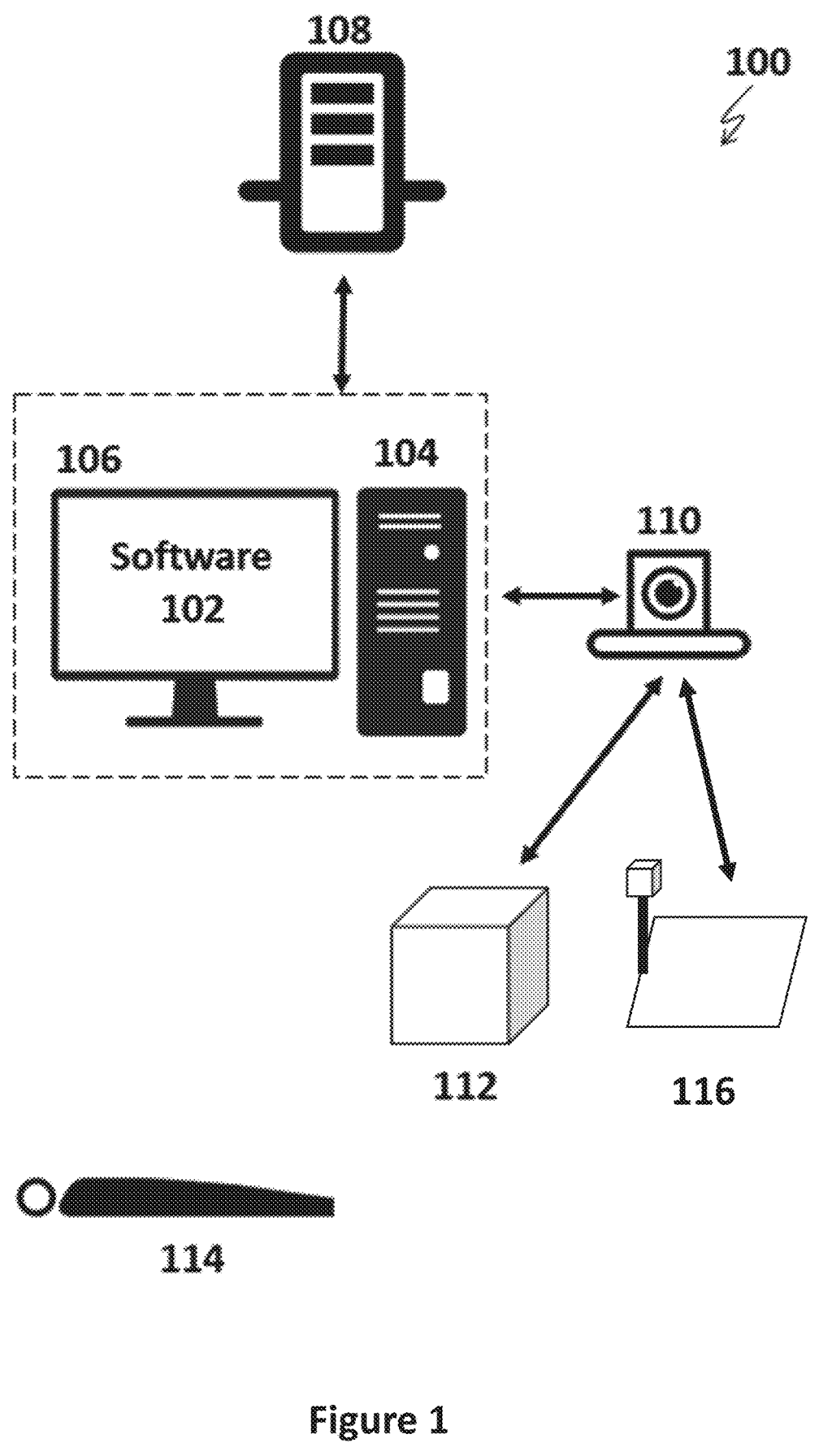

Referring now to FIG. 1 showing a schematic representation of an exemplary ultrasound simulation system 100, according to some embodiments of the invention. In some embodiments, the ultrasound simulation system 100 comprises a software 102 to be used in an electronic device 104. In some embodiments, the electronic device 104 comprises and/or is connected to a screen 106. In some embodiments, the software is saved in the electronic device 104 itself. In some embodiments, the software is saved in a server 108 and it is accessed through the electronic device 104 and shown in the screen 106. In some embodiments, the electronic device 104 comprises and/or is connected to a camera 110. In some embodiments, the system comprises at least one external reference element 112 (see below). In some embodiments, the system comprises an augmented reality (AR) activator (referred hereinafter as 'AR activator') 116 (see below). In some embodiments, the system optionally comprises a complete or partial artificial human body 114 or any other dedicated surface, for example a mannequin or a flat surface, used by the user to perform the virtual ultrasound examinations, as will be further described below.

In some embodiments, the electronic device 104 is a personal computer comprising a screen 106 and a camera 110 with a dedicated access the Internet. In some embodiments, the electronic device 104 is one or more of a tablet, a cellphone, a laptop, a PC or any other compatible electronic device that comprises a screen 106, a camera 110 and access to the software 102 and the server 108.

In some embodiments, a potential advantage of the ultrasound simulation system of the invention is that it does not require specialized hardware, which potentially provides a cheaper system when compared to system comprising dedicated hardware.

Exemplary Reference Element

Referring now to FIGS. 2a-b showing schematic representations of an exemplary reference element 112, according to some embodiments of the invention.

In some embodiments, an exemplary external reference element is a physical object comprising one or more reference markings. In some embodiments, the software 102 of the system 100 is configured to recognize the markings on the reference element 112 by analyzing the visual information received from the camera 110.

In some embodiments, an exemplary reference element 112 comprises any geometrical form. In some embodiments, the geometrical form comprises a 2D form. In some embodiments, the geometrical form comprises a 3D form. In some embodiments, as shown for example in FIGS. 2a-b, the 3D geometrical form of the exemplary reference element 112 is a cube. In some embodiments, the 3D geometrical form of the exemplary reference element 112 can be other than a cube, for example one or more of a sphere, a cylinder, a torus, a cone, a cuboid, a triangular pyramid, a square pyramid, an octahedron, a dodecahedron, an icosahedron, etc. In some embodiments, the 3D geometrical form of the exemplary reference element 112 is a hexagonal prism, as shown for example in FIG. 2e (see also below description about reference element having hexagonal prism form). In some embodiments, the 3D geometrical form of the exemplary reference element 112 may comprise any form as long as it comprises the necessary reference markings.

Returning to FIGS. 2a-b, the exemplary reference element 112, shown for example as a cube, comprises six distinct reference markings in the form of Greek alphabet letters: alpha ($\alpha$), beta ($\beta$), gamma ($\gamma$), delta ($\delta$), epsilon ($\varepsilon$) and theta ($\theta$). It should be understood that these are just exemplary reference markings and that other forms of reference markings maybe used, for example, figures, lines, barcodes, etc.

Figure 2C:
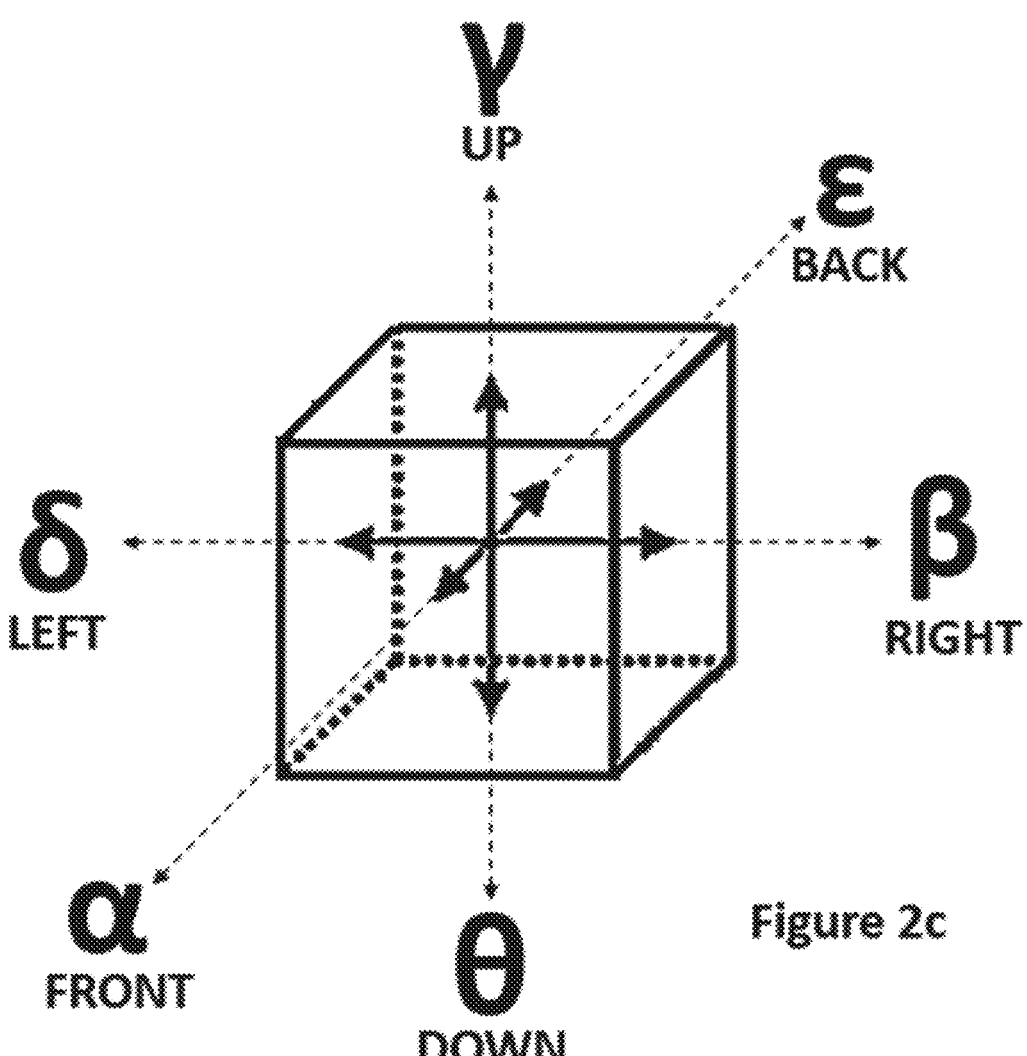

In some embodiments, the software 102 comprises instructions for recognizing the reference markings and providing dedicated directions in the 3D space (for example up, down, front, back, right, left), as shown for example in FIG. 2c.

Figure 2D:
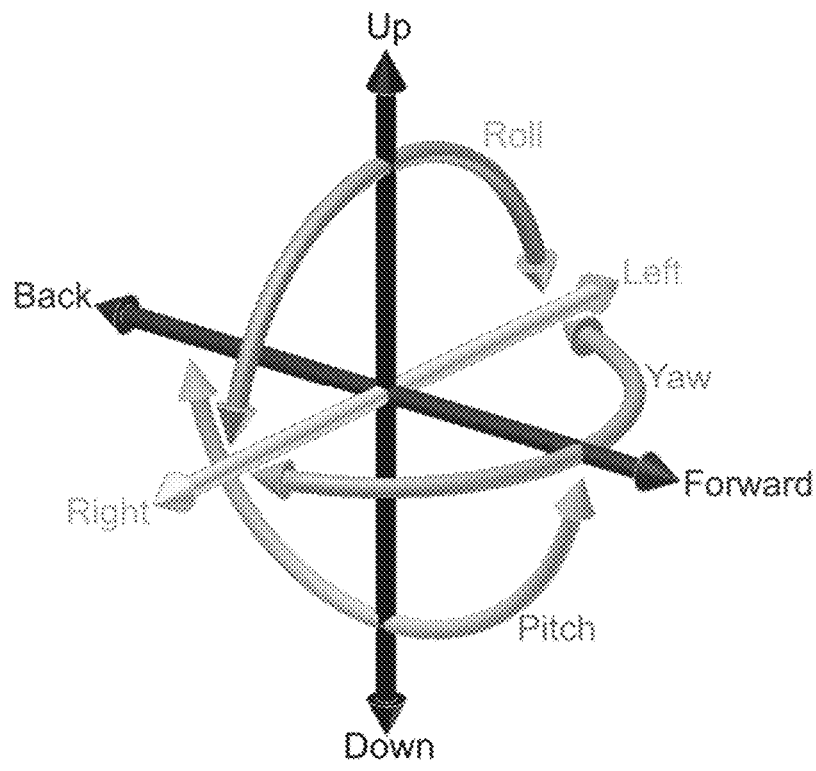

In some embodiments, using the directions as shown in FIG. 2c, the software 102 of the system 100 extrapolates movements of the exemplary reference element 112 in space (spatial movements). In some embodiments, exemplary movements in space are schematically shown in FIG. 2d. In some embodiments, movements in space are one or more of up, down, forward, back (backwards), right, left roll, yaw and pitch.

In some embodiments, the software 102 utilizes at least one reference markers to extrapolate the spatial movement of the reference element 112. In some embodiments, one reference marker is enough for the software 102 to extrapolate the spatial movements of the reference element 112. It should be understood that the use of more markers to extrapolate the spatial movements of the reference element are included in the scope of the invention.

Exemplary Reference Element Having Hexagonal Prism Form

Figure 2E:
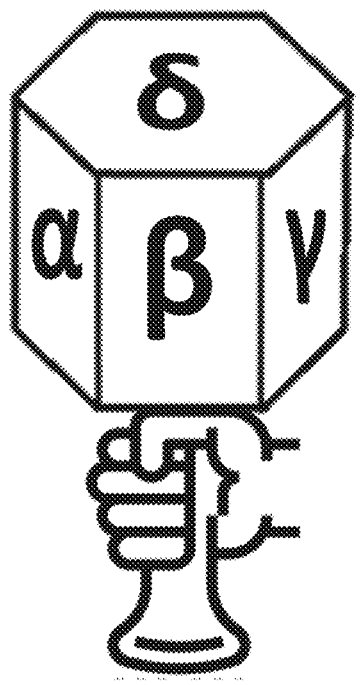
FIG. 2e is a schematic representation of an exemplary reference element having a hexagonal prism form, according to some embodiments of the invention.

In some embodiments, the reference element 112 comprises a 3D form of a hexagonal prism, as shown for example in FIG. 2e. In some embodiments, the inventors have found that a reference element having a hexagonal prism form provides enough surfaces (with markings) for the system to allow a highly precise identification of the reference element in the space and highly precise tracking performance of the reference element, both with minimal or low computational effort.

In some embodiments, as mentioned above, the system is configured to identify the markers on the reference element using a camera. In some embodiments, once the markers are identified, the system locks on them and uses the perceived movements of the markers (changes in spatial location of the markers in space) to translate them into virtual movements of a transducer to then shown the right ultrasound images on the display. In some embodiments, there is a direct correlation between the number of markers found by the system and the computational effort required to follow them and translate them into the right virtual position of the transducer to then associate this information to the images in the library and show the correct image in the display. In some embodiments, the more markers there are, the more computational effort is required and vice versa. In some embodiments, additionally, there is a direct correlation between the number of reference markers and the precision which the system translates the real-world movements of the reference element into virtual transducer ones. In some embodiments, the more markers there are, the more precise is the tracking and vice versa. In some embodiments, as mentioned above, the inventors have found that the optimal number of reference markers, each located on a specific surface, for allowing a highly precise tracking with minimal computation effort is provided by using a reference element having a hexagonal prism form. It should be understood that the invention is meant to cover those embodiments where computational effort is not an issue, for example by using a supercomputer and/or a quantum computer, where the reference element can have as many markings as desired and can have any geometrical form, including a sphere (which has no distinguishable surfaces but one continuous surface).

Exemplary Identification Markers on the Reference Element

In some embodiments, the reference element 112 comprises an additional marking, which is not related to the orientation role of the markings, which provides a unique identification to the user. In some embodiments, identification markers allow the system to access the personal file of the specific user and display/provide/update/upload the relevant file/program to that specific user. In some embodiments, at the first use, the user will be required to link a specific identification marker, optionally irreversibly attached to a specific reference element, to his user account. In some embodiments, when a user has multiple reference elements, for example different reference elements to practice different ultrasound techniques on different places (for example vaginal or abdominal), each reference element will have a specific identification marker, and all identification markers will be linked to the same account.

Exemplary Feedback Mechanisms on a Reference Element

In some embodiments, the reference element comprises on or more feedback mechanisms configured to transmit a type of feedback to the user while using the system. In some embodiments, exemplary feedback mechanisms are one or more of lights, vibration and sounds. For example, the reference element might comprise a plurality of lights that are activated during the use of the system. In some embodiments, when the user is moving the reference element as expected by the system, the reference element will show green lights. In some embodiments, when the user is moving the reference element not as expected by the system, the reference element will show red lights. In some embodiments, using this example, when the user is moving the reference element as expected by the system, the reference element will not vibrate and/or will not sound any sounds. In some embodiments, when the user is moving the reference element not as expected by the system, the reference element will vibrate and/or will sound sounds. It should be understood that the above are just examples to allow a person having skills in the art to understand the invention and that other and/or different uses of the feedback mechanisms are also included within some of the embodiments of the invention.

In some embodiments, on the reference element there are one or more buttons configured to activate and/or actuate features in the system, for example activate the communication between the reference element and the electronic device, begin the simulation, end the simulation, activation of "PRINT" button on the GUI, opening a control panel of the system, commence calibration of the system and other. It should be understood that other actions are also included in the scope of some embodiments of the invention, and that the abovementioned examples are just examples to allow a person having skills in the art to understand the invention.

Exemplary AR Activator 116

Figure 2F:
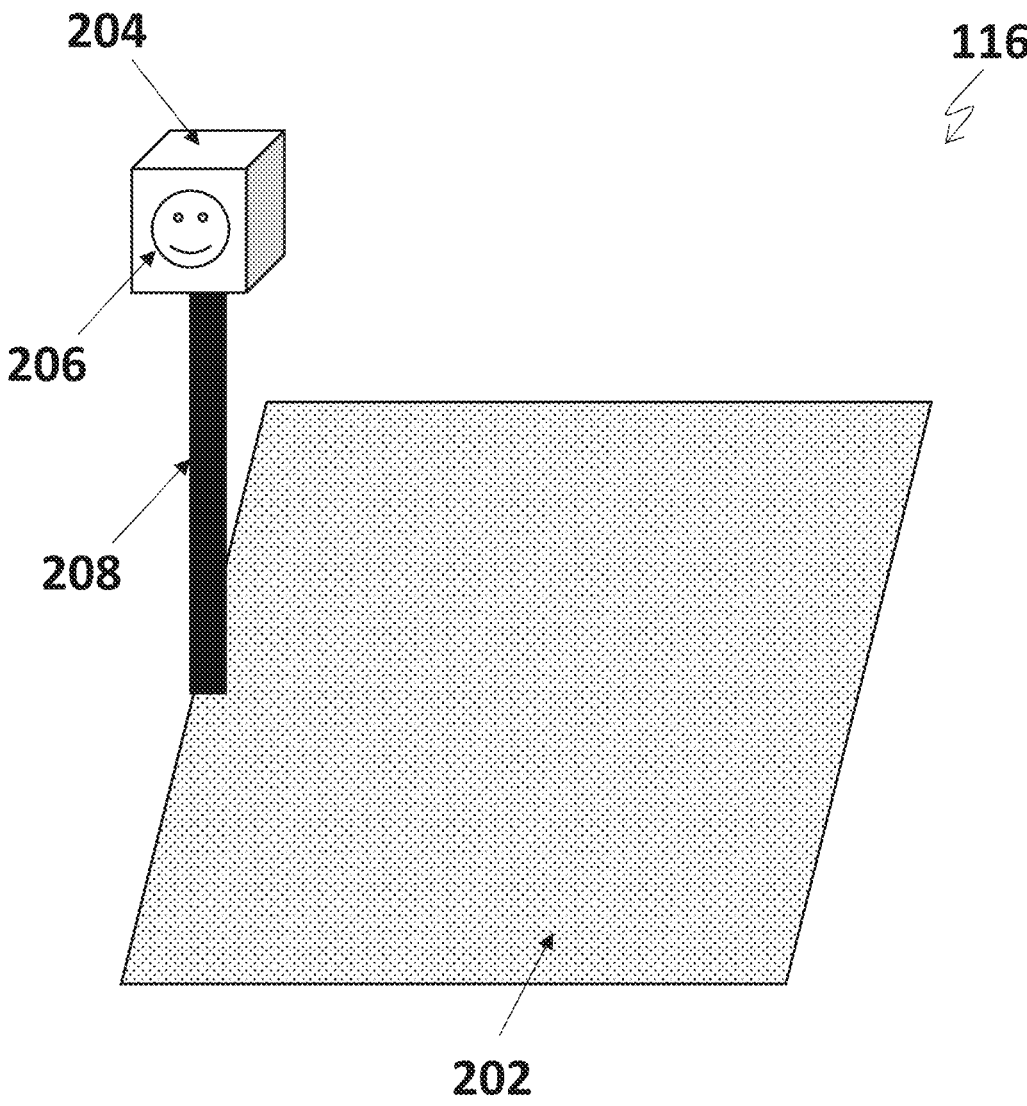
FIG. 2f is a schematic representation of an exemplary AR activator, according to some embodiments of the invention.
Figure 2G:
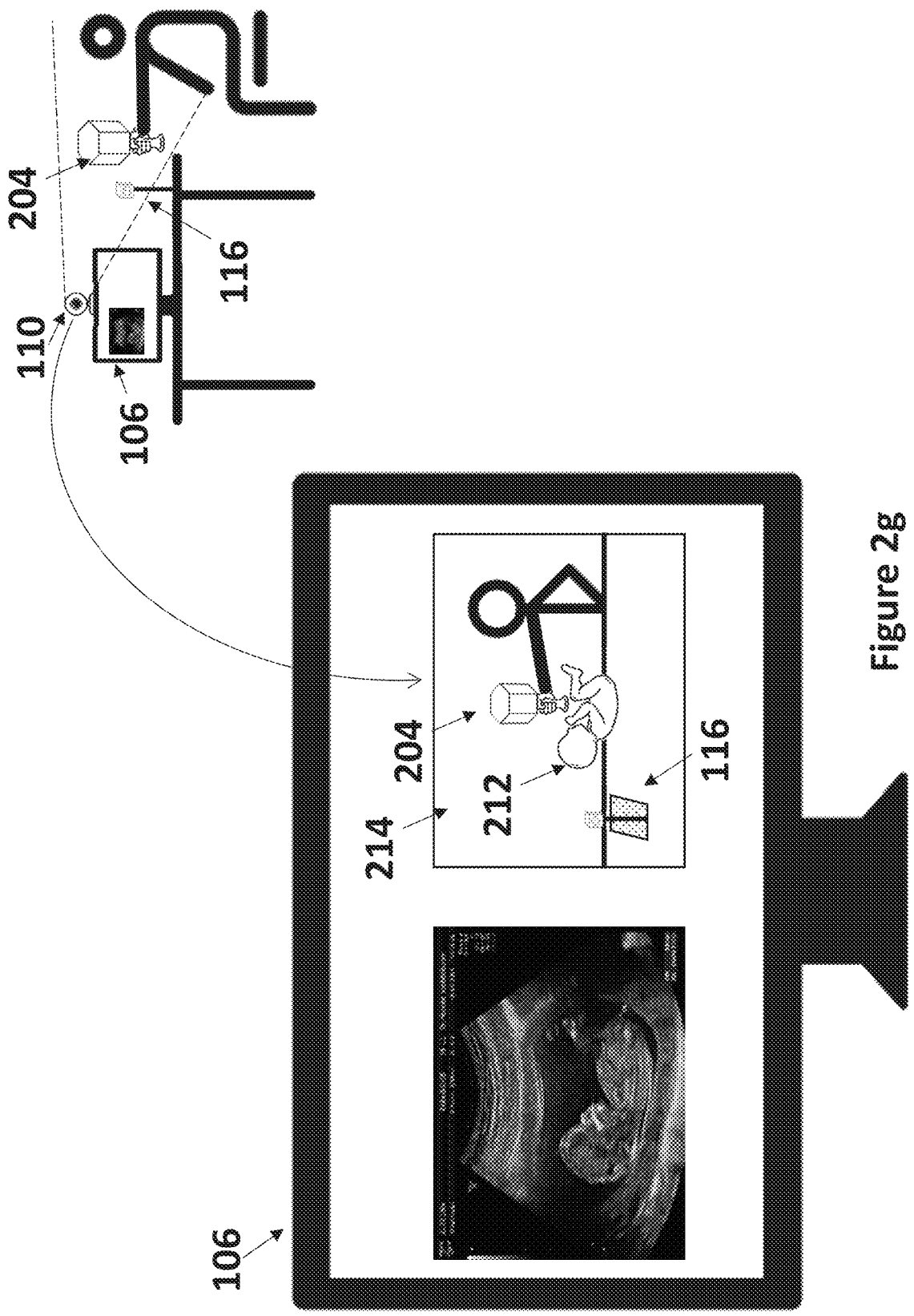
FIG. 2g is a schematic representation of a user using a camera and a screen to visualize AR images during a training session, according to some embodiments of the invention.
Figure 2H:
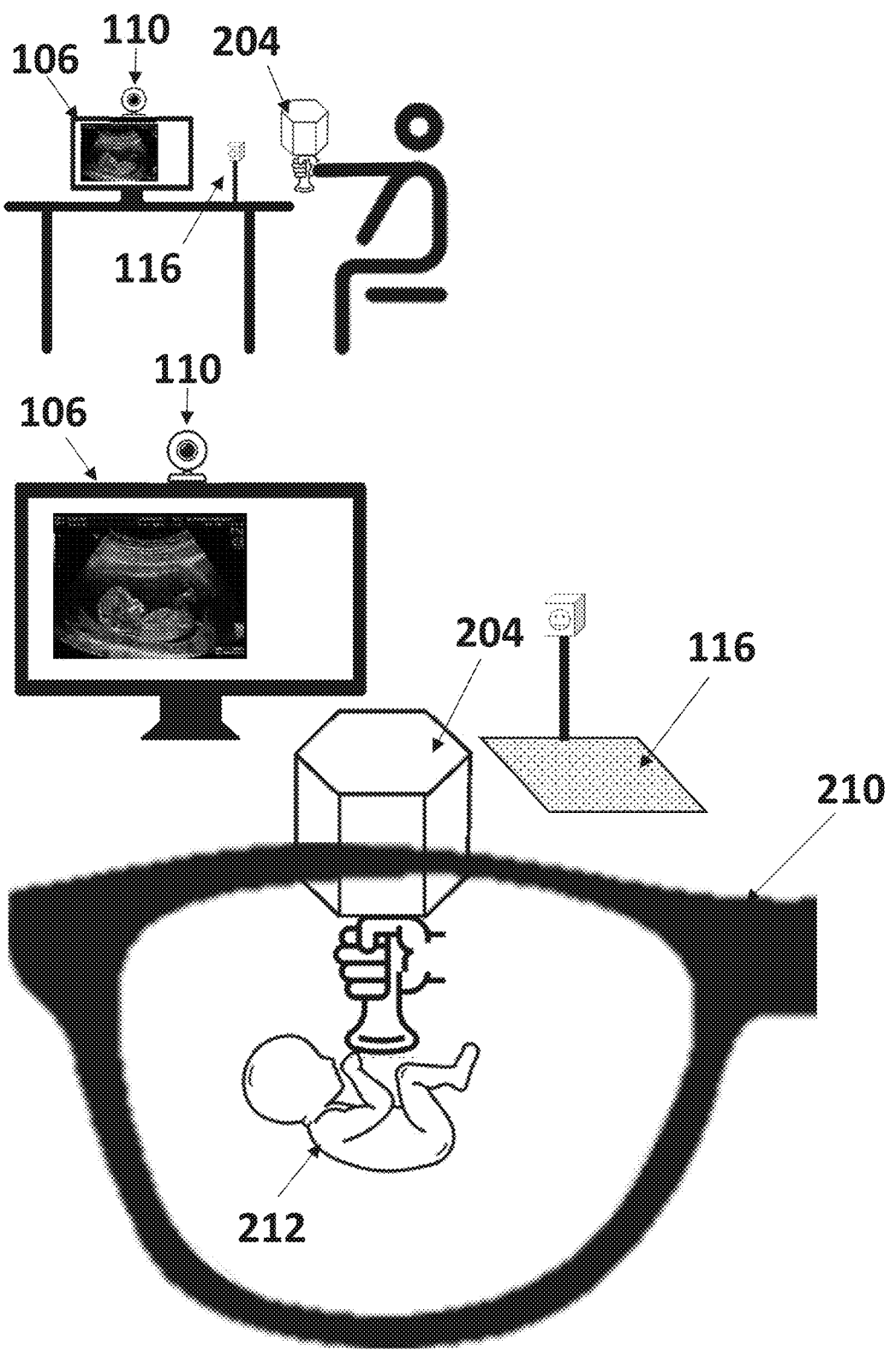
FIG. 2h is a schematic representation of a user using smart glasses to visualize AR images during a training session, according to some embodiments of the invention.

Referring now to FIGS. 2f and 2g showing a schematic representation of an exemplary AR activator 116 and a schematic representation of a user using a camera and a screen to visualize AR images during a training session, according to some embodiments of the invention. In some embodiments, the system further comprises an AR activator 116 used by the system to generate a tridimensional image 212 to be displayed in the screen 106 in concomitance with the real world image 214 captured by the camera 110. In some embodiments, the AR activator 116 optionally comprises a flat surface 202 (for example a pad), optionally having known dimensions, and the AR activator 116 comprises a form, for example, of a cube 204 having a dedicated AR activator image 206, which is identifiable by the system. In some embodiments, the AR activator 116 is positioned on a foldable arm 208, which is irreversibly attached to the flat surface 202. In some embodiments, the AR activator 116 is any AR activator image 206 presented to the system and configured to be used by the system to activate the AR function. In some embodiments, at the beginning of a training session, the system (using the camera 110) acquires the AR activator image 206 of the AR activator 116 and generates a tridimensional image 212 on top of the real world image 214 captured by the camera 110 and displayed in the screen 106. In some embodiments, the tridimensional image 212 is used by the user to help him orientate the reference element 204 in space as he performs the training. Referring now to FIG. 2g, showing a schematic representation of a user using smart glasses 210 to visualize AR images during a training session, according to some embodiments of the invention. In some embodiments, when dedicated smart glasses 210 are used, the tridimensional image 212 is shown on the glasses 210 as an augmented reality object while the system shows the relevant image on the screen 106, which as mentioned before, helps the user orientate and perform the training. In some embodiments, the augmented reality image can be displayed in one or more of a display, a display on top of a real world image capture by the camera, a smart electronic device and a display on a smart glasses.

In some embodiments, the system comprises a library of Augmented Reality data. In some embodiments, the AR data is categorized according to levels of expertise of the trainees. For example, to novice trainees a simplified AR image will be shown, while for experienced trainees, a more complex AR will be shown, for example, showing more anatomical details.

Exemplary Method of Translation Between Markers and Movement

Figure 3A:
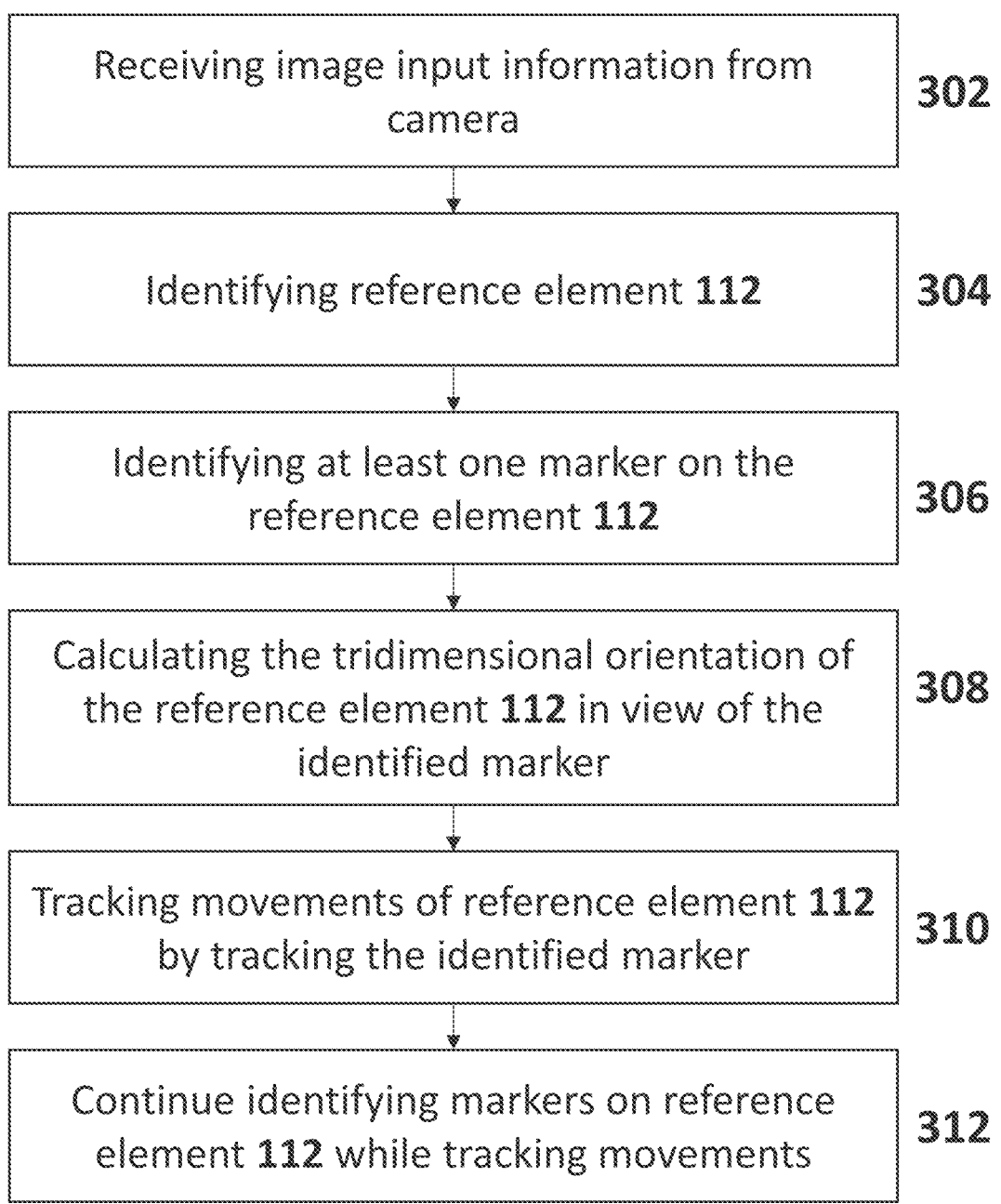
FIG. 3a is a flowchart of an exemplary general method of identification, tracking and translation of movements of the reference element by the software, according to some embodiments of the invention.

In some embodiments, identification, tracking and translation of movements of the reference element 112 is performed using known methods known in the art. For simplicity, an exemplary general method of identification, tracking and translation of movements of the reference element 112 will be shortly explained. Referring now to FIG. 3a, showing a flowchart of an exemplary general method of identification, tracking and translation of movements of the reference element 112 by the software 102, according to some embodiments of the invention. In some embodiments, the exemplary general method of identification, tracking and translation of movements of the reference element 112 by the software 102 is as following:

a. Receiving image input information from the camera (302).

b. Identifying reference element 112 (304).

c. Identifying at least one marker on the reference element 112 (306).

d. Calculating the tridimensional orientation of the reference element 112 in view of the identified marker (308).

e. Tracking movements of reference element 112 by tracking the identified marker (310).

f. Continuing identifying markers on reference element 112 while tracking movements (312).

Exemplary Method of Translation Between Reference Element and Ultrasound Image

Figure 3B:
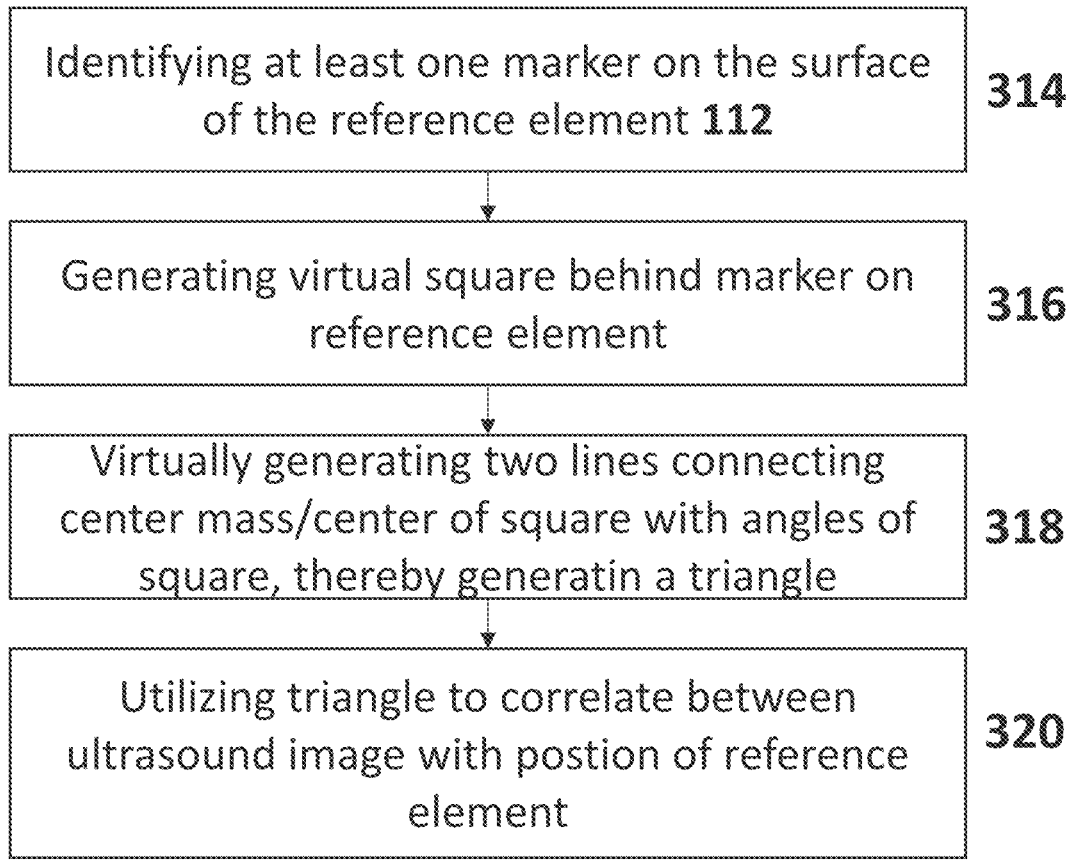
FIG. 3b is a flowchart of an exemplary method of translation between reference element and ultrasound image, according to some embodiments of the invention.

Referring now to FIG. 3b showing a flowchart of an exemplary method of translation between reference element and ultrasound image, according to some embodiments of the invention; and to FIGS. 3c-h showing schematic representations intended to help explain the exemplary method of translation between reference element and ultrasound image, according to some embodiments of the invention.

In some embodiments, the reference element is used for the visualization of ultrasound data, as will be further explained below. In some embodiments, once the software has identified the reference element, as explained above, the software performs a series of virtual actions in order to enable the translation of the spatial information received from the reference element to the correct ultrasound data to be displayed.

Figures 3C, 3D:
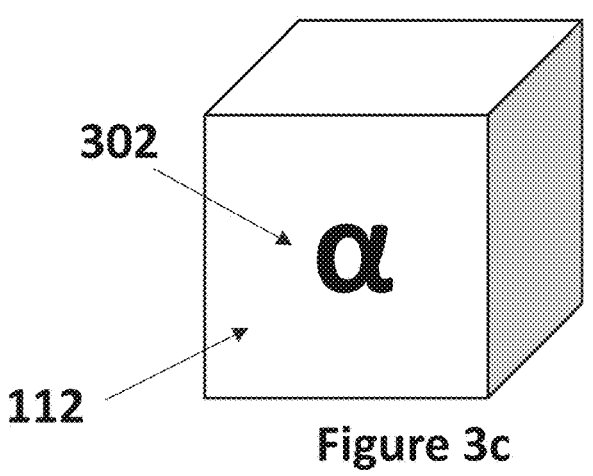
Figure 3F:
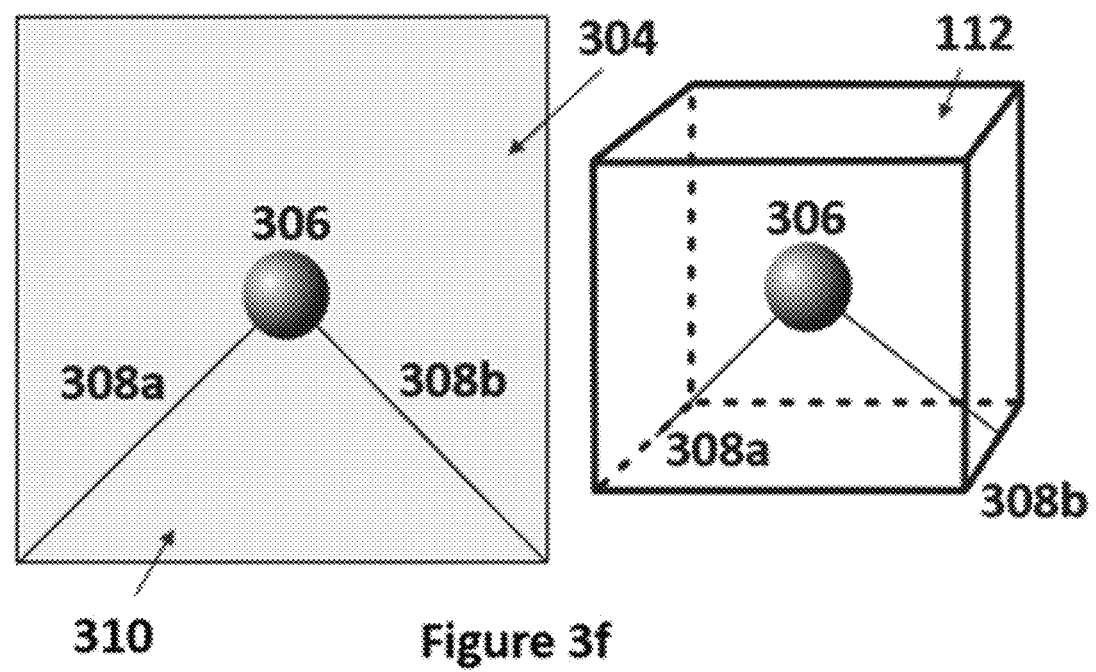
Figure 3G:
Figure 3H:
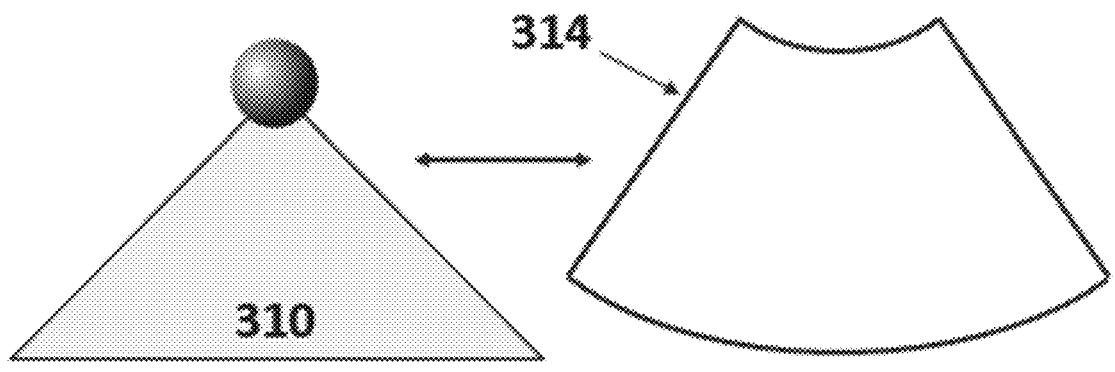

In some embodiments, the software identifies at least one marker 302 on the surface of the reference element 112 (314 in FIG. 3b) and schematically shown in FIG. 3c. In some embodiments, the software generates a virtual square 304 behind the identified marker 302 at the center mass of the reference element 112 (316 in FIG. 3b) and schematically shown in FIG. 3d. In some embodiments, the generated virtual square is used to monitor the movements of the specific marker that was identified to generate it. In some embodiments, these steps are repeated as necessary to generate virtual squares for all markers located on the reference element. In some embodiments, the center of the virtual square 306 corresponds with the center of the mass 306 of the reference element, as schematically shown in FIG. 3e. In some embodiments, from the center of the virtual square 306, the software virtually extends two lines 308a-b from the center 306 towards the lower angles of the virtual square 304 (318 in FIG. 3b) and schematically shown in FIG. 3f. In some embodiments, the system is configured to calculate the length of the virtually extended lines 308a-b and the size of the angles of the virtual square 304. In some embodiments, extension of the two lines 308a-b to the angles generates a virtual triangle 310 where one edge is located at the center 306 and two others at the angles of the virtual square 304. FIG. 3g shows an exemplary ultrasound image 312, and within an exemplary schematic form of the ultrasound image 314. Due to the nature of the ultrasound devices, an exemplary form of the image of the ultrasound is as shown in FIG. 3g marked as 314. In some embodiments, the software utilizes the virtual triangle 310 to correlate with the ultrasound image 312, utilizing the exemplary form of the ultrasound image 314 and the edges of the triangle 310 as reference points, (320 in FIG. 3b) and schematically shown in FIG. 3h.

Exemplary Server, Ultrasound Library Database and its Content

In some embodiments, as mentioned above, the software 102 is in communication with a server 108. In some embodiments, the server comprises an ultrasound library database comprising ultrasound data. In some embodiments, the ultrasound library database comprises one or more of: ultrasound images, sequential ultrasound images, ultrasound videos and tridimensional ultrasound volumes. In some embodiments, the information collected in the ultrasound library database is data that has been processed to comprise tridimensional correlation data, as will be further explained below. In some embodiments, each ultrasound data comprises information regarding the specifics of the ultrasound examination, for example, one or more of: ultrasound operational data, reason for performing ultrasound, date, sex of the patient, medical historical data, organ being scanned, measurements performed during the ultrasound, diagnosis, type of transducer, type and/or brand of device and tridimensional orientation of the transducer over time.

Exemplary Software

Figure 4A:
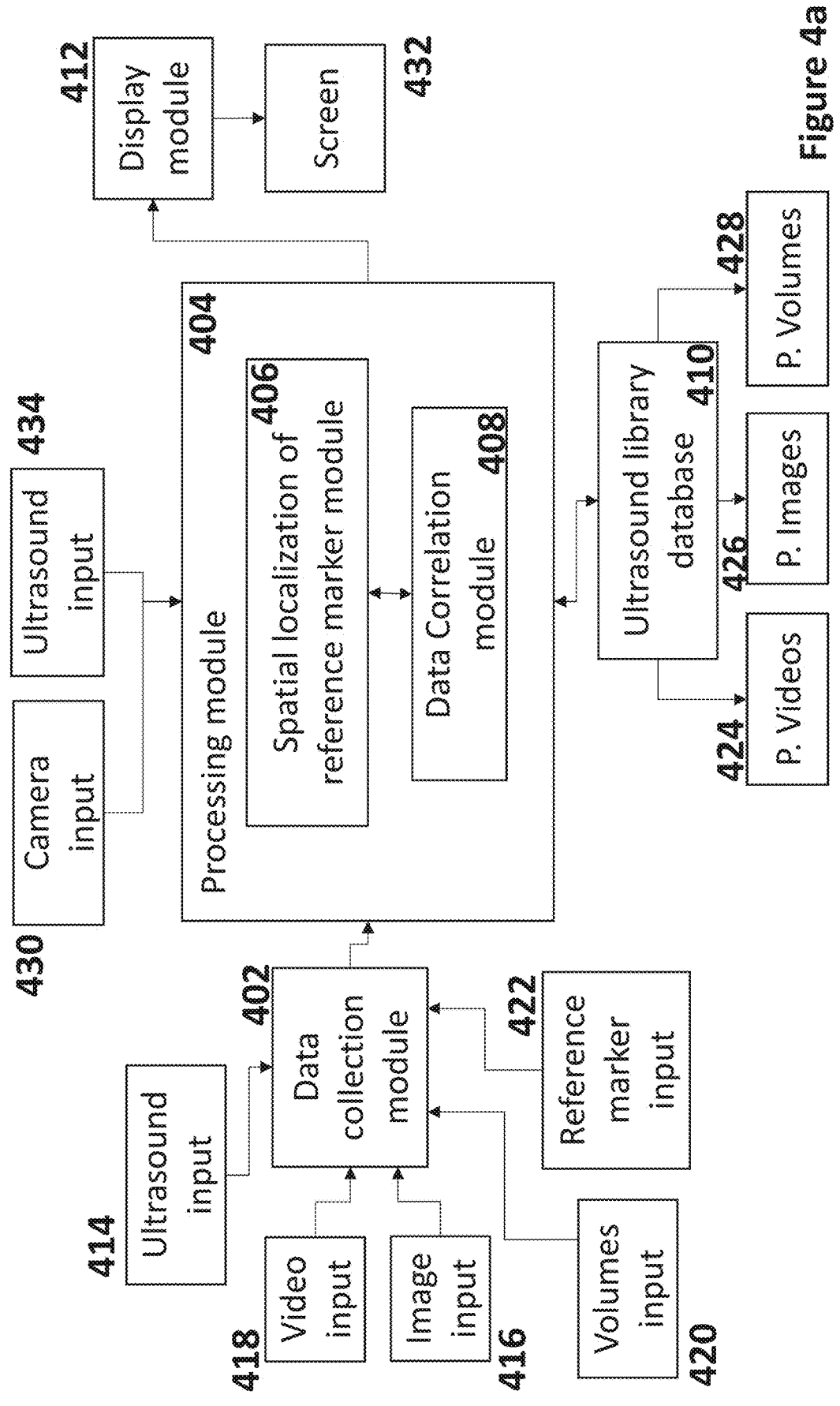
FIG. 4a is a schematic representation of the architecture of the software, according to some embodiments of the invention.

Referring now to FIG. 4a showing a schematic representation of the architecture of the software 102, according to some embodiments of the invention. In some embodiments, the software comprises 4 main parts: a data collection module 402, a processing module 404 that comprises a spatial localization of reference marker module 406 and a data correlation module 408, the ultrasound library database 410 and a display module 412.

Exemplary Data Collection Module 402

In some embodiments, the data collection module 402 is configured to receive external ultrasound data and using the data correlation module 408 in the processing module 404 the external ultrasound data is converted into processed ultrasound data comprising tridimensional correlation data for a reference element. In other words, all external ultrasound data is modified to comprise information about how the transducer was positioned and moved during the ultrasound examination, optionally in relation to the tridimensional spatial information of the patient on which the ultrasound examination were made. For example, how the ultrasound examination was acquired were made in relation to the information of how the patient was laying on a bed.

Exemplary Sources of External Ultrasound Data

In some embodiments, types of external ultrasound data are one or more of the following:

Dedicated Ultrasound Examinations for the Ultrasound Library Database

In some embodiments, dedicated ultrasound examinations 414 are taken to populate the database with ultrasound data. In some embodiments, ultrasound examinations are performed in conjunction with a camera and a reference element attached to an ultrasound transducer 422. In some embodiments, during the ultrasound examinations, the camera records the movements of the reference element that is attached to the ultrasound transducer, while recording the images received from the transducer itself. In some embodiments, the user marks the beginning of the record and the software 102 saves the ultrasound examination with a correlation of the spatial location of the reference element located at the transducer. In some embodiments, the software saves the ultrasound examination in a plurality of formats, like images, videos and/or volumes and/or integration thereof in the ultrasound library database 410. In some embodiments, relevant information related to the examination (see above) is added to the ultrasound data.

Figure 4B:
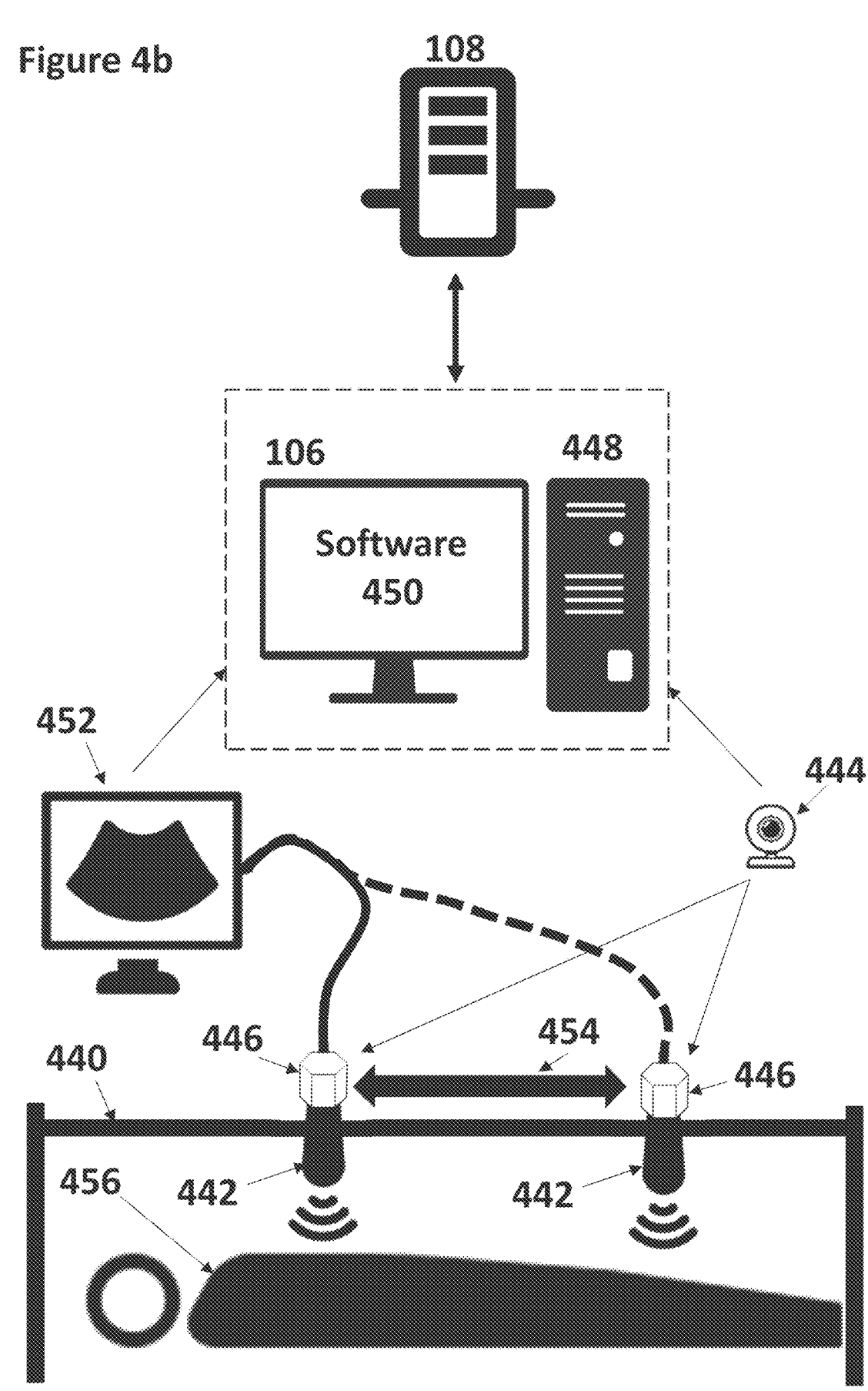
FIG. 4b is a schematic representation of a robotic ultrasound scanner system, according to some embodiments of the invention.

Exemplary Dedicated Robotic Scanner to Populate the Ultrasound Libraries of the Database Referring now to FIG. 4b, showing a schematic representation of a robotic ultrasound scanner system, according to some embodiments of the invention. In some embodiments, the ultrasound libraries of the database are populated with ultrasound scans performed by a dedicated robotic ultrasound scanner system. In some embodiments, the robotic ultrasound scanner system comprises a robotic arm 440 configured to perform movements of a transducer. In some embodiments, the robotic arm 440 is an actual robotic arm (not shown). In some embodiments, the robotic arm is a transducer holder mounted on one or more mechanical rails (schematically shown in FIG. 4b) configured to performed movements in one, two three or more axes. In some embodiments, the mechanical arm is configured to hold one or more transducers 442. In some embodiments, the user can chose the type of transducer according to the desired scan to be performed. In some embodiments, the robotic ultrasound scanner system comprises a camera 444 configured to acquire the movements performed by the transducer 442 and/or a reference element 446 located on the transducer 442. In some embodiments, the robotic ultrasound scanner system comprises a main computer 448 comprising the necessary hardware (i.e.: screen 106) and a dedicated scanning software 450 comprising instructions to actuate the robotic arm 440, the camera 444, optionally the ultrasound equipment 452 comprising the transducer 442. In some embodiments, the computer 448 and the ultrasound equipment 452 are unified in one unit. In some embodiments, scans performed by the robotic ultrasound scanner system are uploaded to a server 108 and/or cloud. In some embodiments, the robotic scanner is configured to perform linear scans (as schematically shown by arrow 454) at a uniform rate. In some embodiments, different types of ultrasound transducers 442 are reversibly connected to the robotic scanner 440. In some embodiments, the user sets parameters of the scan, for example, parameters of speed and/or distance of movement and/or type of transducer, two-dimensional images are collected while concomitantly generating volume files (not shown). In some embodiments, during the scanning process, the transducer 442 connected to the robotic scanner 440 is identified by an external camera 444. In some embodiments, a dedicated reference element 446 with a number of reference images (reference images not shown) that can be identified and spatially monitored are mounted on transducers. In some embodiments, during the scanning, the robotic ultrasound scanner system monitors and records the spatial position of the transducer 442 (or the reference element 446 mounted on the transducer 442). In some embodiments, each ultrasound image generated by the transducer 442 and recorded by the robotic ultrasound scanner system is correlated with the spatial position of the transducer 442/reference element 446 at the moment of the ultrasound recording as acquired by the camera 444. In some embodiments, the volume created is defined by the external coordinates of the transducer 442/reference element 446 recorded by the system using the camera 444 and/or additional cameras (not shown) in order to correlate the recorded volume with a "space" and location of the recording on the "patient" 456 (the person in which the ultrasound recordings are being made). In some embodiments, as mentioned above, the 2D images recorded during the scanning undergo processing to generate a volume image file. In some embodiments, a potential advantage of the robotic ultrasound scanner system is that it potentially allows collection of volumes having a higher quality than solutions of three-dimensional commercial transducers available on the market.

In existing ultrasound devices, 2D ultrasound images are produced in high quality and a plurality of features are allowed. When a 3D image is requested, the existing ultrasound system automatically reduces the quality of the image and blocks the additional features that are allowed when taking 2D images, thus providing a low quality 3D image. The reason existing ultrasound devices do this is because it will require high amounts of computational resources and time to provide a 3D image with all the plurality of features. In some embodiments, the present invention utilizes mainly a two-dimensional transducer that is moved at a constant time and distance, thus allowing an optimal scanning quality, to collect only 2D images that are then used for the generation of a higher-quality three-dimensional volume. In some embodiments, the robotic ultrasound scanner system enables the production of three-dimensional volumes with the help of only two-dimensional transducers, even in devices that do not support the generation of native three-dimensional images. In some embodiments, a plurality of volumes generated by the robotic ultrasound scanner system can be "connected" (unified into one or more volumes) to each other using the external coordinates assigned to them, and this because they are all referenced to the same set of coordinates used during the recording with the camera, for example referenced to one or more of the transducer 442, the reference element 446 and/or any other external reference used during the scans. In some embodiments, each scanned volume is "tested" to assess if the recorded coordinates of the current recorded volume match other recorded coordinates/volumes. In some embodiments, a potential advantage of this is that it potentially ensures the correlation and connection of different volumes for the unification and generation of complex volumes.

In some embodiments, the robotic ultrasound scanner system comprises a feature that allows the user to choose points of interest (or sections of interest) that were recorded during the scan and then convert scans into movies that can be later displayed during training sessions. In some embodiments, videos can also be of a defined section, in black and white and/or Doppler and/or color Doppler. In some embodiments, the scan products that are possible to be generated using the robotic ultrasound scanner system of the present invention include, for example, a collection of high quality two-dimensional images defined in a system of tested coordinates, as well as videos without transducer motion in the same coordinate system.

In some embodiments, the robotic ultrasound scanner system is configured to work in defined segments, after which, at each stopping point, a video clip is generated and saved. In some embodiments, the generation of videos are performed while images in other segments are still being collected.

In some embodiments, alternatively or additionally, a three-dimensional transducer (not shown) is connected to the robotic arm, on which optionally there is a bracket with stickers that allows a spatial position recognition and recording by the camera of the generated 3D scan. In some embodiments, at each point of interest, the linear scanning is stopped and then the three-dimensional transducer is activated, where a collection is made and saved, and then the linear scanning continues to the next collection point.

In some embodiments, alternatively or additionally, a Doppler transducer (not shown) is connected to the robotic arm, on which optionally there is a bracket with stickers that allows a spatial position recognition and recording by the camera of the generated 3D scan). In some embodiments, at each point of interest, the linear scanning is stopped and then the Doppler transducer is activated, where a collection is made and saved, and then the linear scanning continues to the next collection point. In some embodiments, the Doppler data is color Doppler data.

Exemplary Process of Scans and Volumes by the Robotic Ultrasound Scanner System

In some embodiments, the robotic ultrasound scanner system comprises a dedicated software 450 comprising instructions for building volumes from high-quality two-dimensional ultrasound section images (in a system of "tested" coordinates) collected by the robotic ultrasound scanner system. In some embodiments, the final product is a three-dimensional volume with defined "tested" coordinates tested, where the directionality and/or orientation of the collection is recorded and saved in the system. In some embodiments, the volumes generated by the high-quality two-dimensional ultrasound section images are further provided with relative sizes to allow the user to correctly orientate himself in space, this is because the generated 3D volume does not comprise depth marks, which are usually generated in lower quality native 3D volumes.

In some embodiments, the dedicated software 450 comprises instructions to combine one or more volumes, scans and/or videos to generate a unified collection of ultrasound information of the area that was scanned, which is then used during the training sessions. In some embodiments, the dedicated software robotic ultrasound scanner system 450 comprises instructions to provide responsive display of the volumes, scans, videos and/or unified collection of information given a spatial transducer location, for example, during training sessions using a camera.

In some embodiments, the volumetric information includes layers of volumes, videos and scans, all defined in the same system of coordinates (optionally provided by the system itself and/or the user) and the system comprises a feature that allows an user to manually add volumetric information, for example, measurements, markings and relevant text according to the multiplicity of volumes.

De-Novo Ultrasound Examinations

In some embodiments, previously acquired ultrasound examinations (images 416, videos 418 and/or volumes 420) are inserted using the data collection module 402. In some embodiments, the data correlation module 408 with the processing module 404 extrapolates the estimate spatial location of a reference element and/or a transducer during the ultrasound examination. In some embodiments, the spatial location is referred to one or more fixed dimensions, for example, the orientation of the patient while the ultrasound examination was performed.

Reverse Ultrasound Examination from Reference Element Spatial Information

In some embodiments, recorded and/or in real-time spatial movements of a reference element 422 are used to match already stored ultrasound examinations. In some embodiments, the system utilizes recorded spatial movements of a reference element and searches the database for possible ultrasound examinations that match those recorded movements.

Referring back to FIG. 4a, ultrasound data 434 (images, volumes, etc.) are received into the processing module 404. In some embodiments, the data correlation module 408 extrapolates from the ultrasound data 434 information of how the transducer was positioned and moved during the ultrasound examinations. Then, in some embodiments, the display module 412 shows in the screen 432 a virtual transducer and how it supposedly moved during the ultrasound examination.

Exemplary Ultrasound Library Database 410

In some embodiments, as mentioned above, processed external data received from the data collection module 402 is processed by the data correlation module 408 in the processing module 404 and stored, as processed ultrasound data, in the ultrasound library database 410. In some embodiments, the data stored in the ultrasound library database 410 is one or more of processed ultrasound videos 424, processed ultrasound images 426 and processed ultrasound volumes 428. In some embodiments, as mentioned above, processed ultrasound data comprises the tridimensional correlation data from and for a reference element. In some embodiments, the ultrasound data is indexed in a matter that allows recovery of specific frames according to a unique index identification. For example, ultrasound data related to kidney comprising ultrasound images frames taken from right to left will be indexed so the frame located at the most right side of the data is indexed with a unique index identification, and all following frames following it until the last frame which is in the most left side of the ultrasound data. In some embodiments, unique index identifications are used for one or more of: directing, instructing and/or showing a user a specific ultrasound data frame and provide instructions to the system on what to show. It should be understood that these are just examples, and other uses for unique index identifications are also included in the scope of some embodiments of the invention. In some embodiments, the system allows the identification of internal organs shown in the ultrasound data by either image processing (with or without the use of AI systems) and/or by manual insertion of information before and/or during the indexing of the ultrasound data.

Exemplary Processing Module 404

In some embodiments, in general, the processing module 404 is responsible for the transformation and/or enhancement of one or more types of information from one or more of the data collection module 402, camera input 430 and ultrasound input 434 and to perform one or more of storing the transformed/enhanced information in the database 410 and/or provide a visual output through the display module 412 on a screen 432.

In some embodiments, the processing module 404 comprises one or more of a spatial localization of reference marker module 406 and a data correlation module 408.

Exemplary Spatial Localization of Reference Marker Module 406

In some embodiments, visual information received from a camera (camera input 430) is analyzed by the spatial localization of reference marker module 406, and reference markings are identified on a reference element. In some embodiments, once the reference markings are identified, the spatial localization of reference marker module 406 translates 3D spatial movements of the reference element into data that is correlated, by the data correlation module 408, with relevant modified/enhanced ultrasound data (images/videos/volumes) stored in the ultrasound library database 410, and then the display module 412 shows them in a screen 432.

Exemplary Data Correlation Module 408

In some embodiments, the data correlation module 408 fulfills a dual role, one role during the insertion of modified/enhanced ultrasound data into the ultrasound library database 410, and another role during the displaying of ultrasound images during the use of the system (which will be further explained below).

In some embodiments, during the insertion of modified/enhanced ultrasound data into the ultrasound library database 410, the data correlation module 408 receives regular ultrasound data, for example ultrasound images, ultrasound volumes and/or ultrasound videos and modifies it to achieve enhanced ultrasound data, for example enhanced ultrasound images, enhanced ultrasound volumes and/or enhanced ultrasound videos. In some embodiments, the enhanced ultrasound data comprises relevant information, for example, spatial movements of the transducer when the ultrasound data (image/volume/video) was taken. In some embodiments, the relevant information is used later, together with movements received for example from a reference marker.

In some embodiments, the enhancement of the regular ultrasound data is based on the same principal, which is assigning a spatial allocation of an ultrasound transducer to each "frame" of ultrasound data, as will be further explained below.

Common ultrasound imaging devices visualize a 2D cross-section of a 3D body. Usually, the cross-section is perpendicular to the transducer probe and is of arbitrary orientation since it depends on how the user is holding the transducer. For example, a representation of the 2D cross-section image can be explained as a slicing area 502 of the total volume 504, as shown for example in FIG. 5.

Definitions

In scientific visualization and computer graphics, volume rendering is a set of techniques used to display a 2D projection of a 3D discretely sampled data set, typically a 3D scalar field. A typical 3D data set is a group of 2D slice images acquired for example by an ultrasound, CT, MRI, or MicroCT scanner. Usually these are acquired in a regular pattern (e.g., one slice every millimeter) and usually have a regular number of image pixels in a regular pattern. This is an example of a regular volumetric grid, with each volume element, or voxel represented by a single value that is obtained by sampling the immediate area surrounding the voxel.

Voxel: short for volume element (or also known as volume pixel), it is the smallest unit of a three-dimensional volume equivalent of a pixel in a 2D image.

Volumetric buffer: is the total volume of the 3D body (or a large 3D array) which comprises a plurality of voxels, each of which represents a view-independent 2D cross-section of an ultrasound sample.

An arbitrary slice is a virtual image frame buffer defined in a local independent coordinate system.

In some embodiments, an arbitrary slide is set and the voxels pierced by the virtual frame are sampled, mapped and displayed in their image coordinate system after the virtual image frame is clipped against the volume buffer.

In some embodiments, the algorithm is an extension of the widely known 2D scan-line algorithm where at each scan-line the third dimension is also interpolated.

Figure 6A:
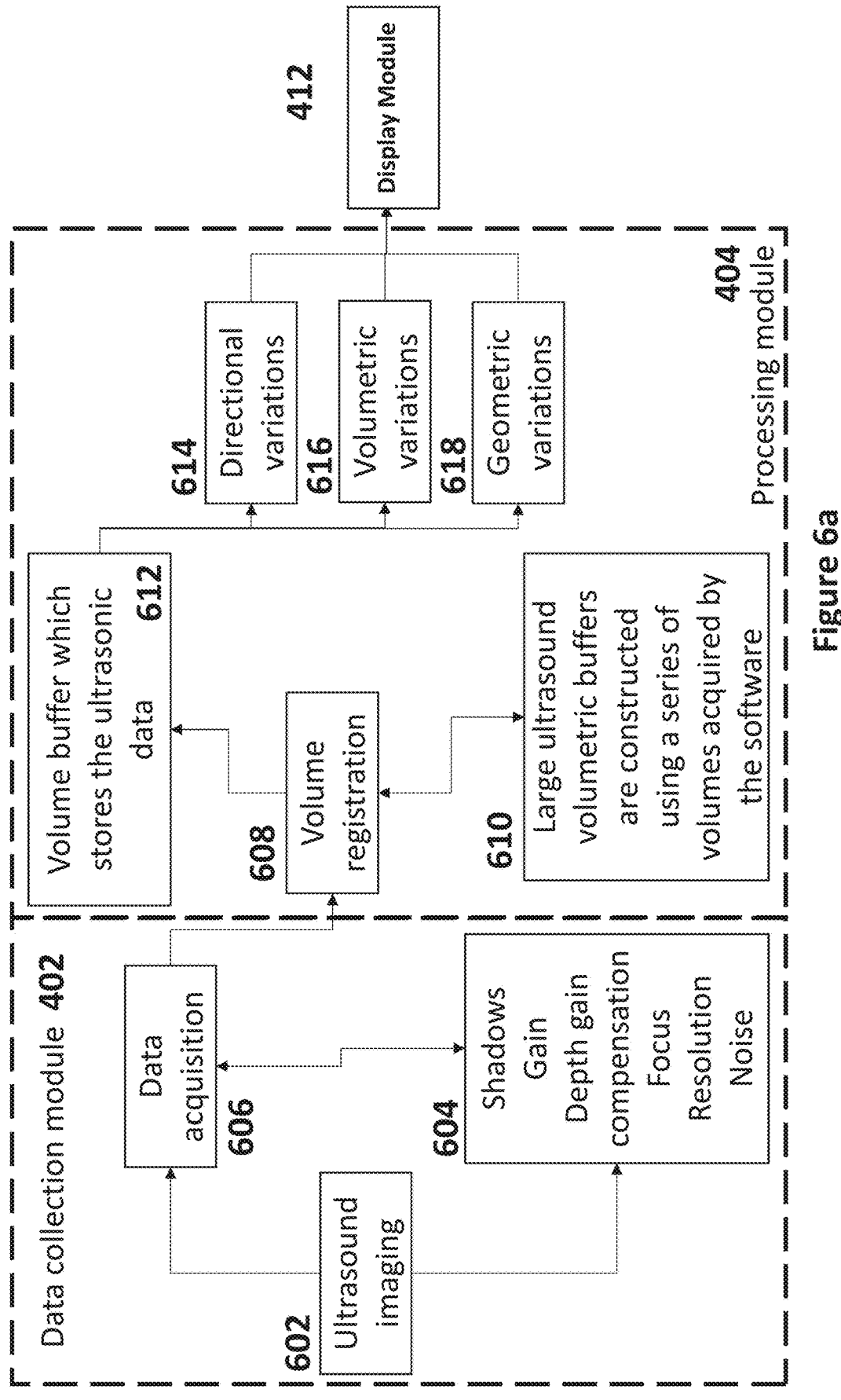
FIG. 6a is a block diagram of exemplary technical issues involved in the field of ultrasound simulation, according to some embodiments of the invention.

Referring now to FIG. 6a showing a block diagram of exemplary technical issues involved in the field of ultrasound simulation and examples of how the system of the invention resolves these technical issues, according to some embodiments of the invention. These were also further described by Aiger et al in *Real-Time Ultrasound Imaging Simulation, Real-Time Imaging* 4, 263-274 (1998), which is incorporated herein in its entirely.

The Principles of Ultrasound Devices

The ultrasound input device is the transducer which is manually positioned by the physician. The transducer converts electric energy into ultrasound energy and vice versa. It produces pulses of sound waves and sends them to the patient's body. It also receives the echos from the patient and converts them to electric energy. This energy is translated into an image that consists of gray level pixels which represent the structure of the body image in the ultrasound display. There are different kinds of transducers at different frequencies with which it is possible to determine the depth and the resolution of the image. The physical principle of the ultrasound is as follows. Pulses of ultrasound, which are short pulses of sound wave at high frequency (1-15 MHz), are generated by the transducer (called pulse beam) and sent into the patient's body. They produce echos at organ boundaries and within tissues. These echos return to the transducer and are detected, processed and translated into appropriate gray level pixels which form the image on the ultrasound display. The gray level is a function of the reflection coefficient of the body at the appropriate location. The reflection coefficient is an attribute of the tissue depending on its physical, chemical and other characteristics. The location of the pixels corresponds to the anatomic location of the echo-generating structure determined by knowing the direction of the pulse when it enters the patient and measuring the time for its echo to return to the transducer. From an assumed starting point on the display, the proper location for presenting the echo can then be derived, provided the direction in which to travel from that starting point to the appropriate distance is known. With knowledge of the speed of sound, the echo arrival time can be converted to distance to the structure that produces this echo.

Ultrasound Imaging 602

In some embodiments, the system, as an ultrasound simulation system, generates images in real-time that resemble real ultrasound images, including the typical ultrasound functions, depth gain compensation (DGC) and gain. In some embodiments, real-time imaging means a frame rate of at least 10 Hz (over 10 frames per second). In some embodiments, the system forms a volume from real ultrasound images (received by the data collection module 402) in an off-line pre-process (in the processing module 404), and then slices the volume (on-line) to display (by the display module 412) a processed image of the oblique slice. In some embodiments, such images can be generated very rapidly, including post-processing enhancements, and can produce images which are, in most cases, indistinguishable from real ultrasound images.

However, the inventors have found that this method of generating images from a pre-sampled ultrasound volume has some inherent problems, due to the fact that an ultrasound image has view-dependent features and an acquisition-parameter-dependent character. This fact is two-fold: firstly, the pre-processed volume dataset includes some unwanted view-dependent features that should be removed. Second, the generated simulated image from a given arbitrary direction should be enhanced and should include the appropriate view dependent features. These and other inherent problems 604 are listed below.

Shadows: In some embodiments, the ultrasound image exhibits shadows when closer objects obscure the sound waves from further objects. In some embodiments, the shadows of a given image are correlated with the specific sampling direction. In some embodiments, this effect is minimized by the software during the data collection, because this feature is not reversible. In some embodiments, the data at the shadow are lost and cannot be recovered unless the same area is sampled from a different viewing direction which views the shadow areas.

Gain: In some embodiments, the Gain control determines how much amplification is accomplished in the ultrasound receiver. In some embodiments, since the Gain operates on the image globally and has a uniform effect on the entire voltage received, it is not correlated with the specific sampling direction. In some embodiments, the Gain is easily simulated, but problematic during data collection. In some embodiments, if the data are sampled with too little Gain, weak echoes are not registered and these echos are lost. On the other hand, in some embodiments, too much Gain causes saturation; that is, most echoes appear bright, and contrast resolution is lost. In some embodiments, since Gain affects the sampling volume in an irreversible manner, therefore the sample is performed with an appropriate Gain level.

Depth gain compensation (DGC): In some embodiments, the DGC equalizes differences in received echo amplitudes as a function of the reflector depth. In some embodiments, reflectors at different depths with equal reflection coefficients produce different return amplitude echoes arriving at the transducer. In some embodiments, echoes are displayed from similar reflectors in a similar way. In some embodiments, the DGC functions as the Gain does, but at different levels as a function of the depth (the distance from the transducer). In some embodiments, the user sets different Gain controls for different depths. In some embodiments, most ultrasound devices can set eight control points which define the DGC behavior. In some embodiments, like the Gain, the DGC is correlated with the sampling direction. In some embodiments, during data collection, given the dependence on the sampling direction, the image is as homogeneous and view independent as possible. In some embodiments, the main problem with DGC and Gain is that they are irreversible, and some data are always lost during the collection and cannot be recovered from the sampled volume. However, in some embodiments, with a good setup of the DGC and Gain levels it is possible to generate a volume buffer from which simulated are get with images almost indistinguishable from real ultrasound images.

Focus: In some embodiments, the width of the pulse beam generated by the transducer increases with depth, i.e. the beam has the shape of a cone whose apex is at the transducer. In some embodiments, the pixel resolution is a function of the beam width. Thus, in some embodiments, an ultrasound image exhibits varying resolutions at different depths. In some embodiments, the first problem is to simulate this different resolution based on one sampled volume taken with a specific machine and a specific transducer. Thus, in some embodiments, it is needed to use an ultrasound machine with a narrow beam to get an almost homogeneous sampled volume. In some embodiments, in high end machines the beam size is small and it is neglected in the simulation. In some embodiments, very much like the operation of a camera and the physics of light that passes through lenses, the ultrasound beam can also be focused at an arbitrary field of view. In some embodiments, the focus is set at an arbitrary depth and get the highest resolution at that depth. In some embodiments, the second problem related to focus is to simulate the arbitrary focal depth by changing the resolution at the related focal depth. In some embodiments, one way to do this is to change the sample rate while generating the simulation image depending on the depth of the scan line (see the later section on 'Real-Time image generation'). In some embodiments, multiple focuses use a different pulse for each one of the required focuses, and the generated image has high resolution at several depths. However, in some embodiments, using multiple focuses results in longer refresh rates. In some embodiments, the collection sampling time remains short to avoid the introduction of undesired movements. Thus, in some embodiments, the volume is sampled in a single focus.

Resolution: In some embodiments, the resolution of the acquired data is defined by the user who sets the magnification size. In some embodiments, the acquired resolution is, of course, constant in the sense that it may be either over or under sampled in the on-line process. In some embodiments, during the collection phase the sampled resolution also affects the size of the entire image. In some embodiments, if magnification is applied than we get a smaller area of higher resolution. In some embodiments, this trade-off implies that acquiring data of higher resolution takes more time. In some embodiments, in most cases the sampling is not performed at higher resolution and it is preferred to minimize the collection phase by sampling larger areas. However, in some embodiments, certain pathologies are better learned from a smaller volume of higher resolution. In some embodiments, another related problem is the uneven resolution of the sampled volume. In some embodiments, the x-y slices (the sampled images) have a different resolution to the z-x planes (the inter-slice dimension). In some embodiments, the shape of the ultrasound beam is not symmetric. In some embodiments, it gets wider along the z axis than in the x-y plane (x-y is the ultrasound image plane). Thus, in some embodiments, the x-y planes have a higher resolution than other planes. Our experience shows that this is not an aquatic problem and the resolution variations are hardly noticeable during the simulation.

Noise: In some embodiments, the ultrasound images are very blurred and noisy. However, in some embodiments, this is not a real problem, since the simulation should retain these characteristics. In some embodiments, they are also not view-dependent, and thus these attributes require no special treatment.

It should be understood that the above mentioned are just examples, and that more and/or other functions are changed using one or more buttons provided by the system, and those are also included in the scope of some embodiments of the invention.

In summary, in some embodiments, some of the above ultrasound features (for example DGC, Gain and/or Focus) are alleviated by tuning down the acquisition parameters. However, in some embodiments, it is not possible to remove them in a post-process. In the following section it will be described the on-line imaging process, performed in some embodiments of the invention, in which all the above ultrasound features are simulated over the image with respect to the view direction and in accordance with the user's specific parameters.

Figure 5:
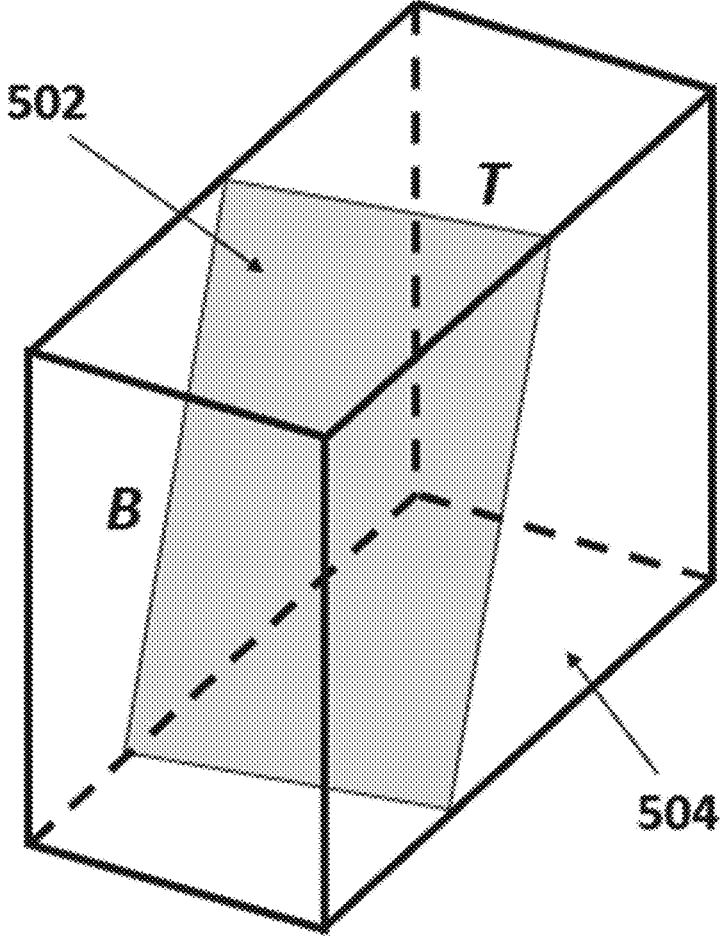
FIG. 5 is a schematic representation of the 2D cross-section image of a total volume, according to some embodiments of the invention.

Real-Time Image Generation:

As explained above, the common ultrasound imaging devices visualize a 2D cross-section of the 3D body. The cross-section is perpendicular to the probe and is of arbitrary orientation. The simulation of this image is basically a slicing algorithm of the volumetric buffer (FIG. 5). The assumption is that the volume buffer is a large 3D array of voxels, each of which represents a view-independent ultrasound sample. The arbitrary slice is a virtual image frame buffer defined in a world coordinate system. The voxels pierced by the virtual frame are sampled, mapped and displayed in their image coordinate system after the frame is clipped against the volume buffer. In many cases the mapping between world and image space does not involve scaling, and the virtual frame can be voxelized with no filtering.

In some embodiments, a voxelization algorithm for planar polygons is used, which is basically an extension of the widely known 2D scan-line algorithm where at each scan-line the third dimension is also interpolated. In some embodiments, a sweeping technique where a polygon can be generated by replicating one discrete line over the other and saving most of the computations involved in the discretization process of the plane is used. In some embodiments, the sweeping technique is fast enough to voxelize slices in real-time on a Pentium processor (a 300×300 voxel slice can be scaled and displayed in a 400×400 pixel image in less than 1 second). However, in some embodiments, when scaling is required, voxel oversampling and filtering are necessarily involved.

In some embodiments, voxelization with scaling calls for the development of fast sampling algorithms of 3D polygons. A brute force oversampling algorithm would use a trilinear interpolation of the dense lattice of sampling points. However, even an incremental computation of the trilinear function along a straight line would not avoid the excess of memory access, much of which is repeated.

In some embodiments, this sampling process should incorporate the Gain and DGC functions, as well as other functions like Focus and casting shadows. The effect of the Gain and the DGC on the image is basically the same. The Gain affects the whole image simultaneously. The DGC function is set by eight potentiometers which control the effect on different areas of the image. The two values are combined to modify the pixel value as a function of its range in image space. Given the four points which define the image frame in the world coordinates, the slicing algorithm scans all the voxels intersected by the frame and maps them to the image coordinate systems.

The following algorithm, as described also by Aiger et al, is based on the weaving method in which the voxelized plane is generated by replicating a voxelized line, called a template, along a base voxelized line. In some embodiments, weaving is a natural technique for voxelizing surfaces which can be obtained by sweeping some fixed curve through space in such a way that the orientation of the swept curve remains unchanged throughout. In some embodiments, the voxelized plane should be free of holes, which means a correct sample of the slice. In some embodiments, weaving can be implemented very efficiently. If $T=X_i, Y_i, Z_i$ are the coordinates of the ith voxel in the template T, then the sequence of offsets from a given reference point, say the template starting point $(T_0)$, is called the template offset form. The offset value $T_i-T_0$ is defined by:

$$dT_i=T_i-T_0=Z_i*(sizeX*sizeY)+Y_i*sizeX+X_i$$

where sizeX and sizeY are the volume array dimensions. In other words, the dT value is the unfolded offset inside a linear volume. The template offset form, denoted by T, is computed once at the outset and stored in an array. Then, for each voxel u in the base, denoted by B, the T array is used to incrementally construct a translate of the template, starting at u. The basic algorithm that maps the voxels to the image buffer, I[i][j]. is a double loop which runs over all the uj values of the base and all the vi values of the template: The inner loop runs over the i while j is constant. A pointer ptr=&(Volume[uj]) is used to further simplify the computation. A clipping process is necessary to avoid overflow of the $T_i$, since the equation above holds for $T_i$ in the volume. This is done by clipping each row (template) against the volume so that the i index runs between the clipped boundary. The clipping cost is insignificant since it is applied only once in a row, while the memory access time to the voxels dominates the cost. Thus, it is most important to minimize the number of retrievals. Note that the preceding statement assumes that there is a one-to-one mapping between the voxel space and the pixel space, which is not necessarily true. The image space resolution is constant and defined by the display size. However, the slice size is defined on-line by the user, who can either zoom in or out. For efficiency, in some embodiments, it is important to avoid unnecessary access to the volume buffer. In some embodiments, the access time to the volume memory is dependent on the volume size, since adjacent voxels in large volumes have longer offsets, which tend to have a low cache hit ratio. In some embodiments, in the case of a zoom out, the voxels are smaller than the pixels. In some embodiments, stepping inside the volume in a pixel-sized step is an under-sampling of the voxels, and yields an image of reasonable quality. In some embodiments, in the case of a zoom in, the voxels are over-sampled and yield a displeasingly blocky and jaggy image. In some embodiments, to avoid the redundant over-sampling of the same voxels, the zoom in image is generated by two interleaved processes. In some embodiments, the first samples the volume, and generates an intermediate image whose pixels are of voxel size. In some embodiments, the other process scales up the image into the final size. In some embodiments, since the image frame is scanned in scan line order, each intermediate row can be stretched before scanning the next row. In some embodiments, then the intermediate image needs to stretched vertically along its column to the final size. In some embodiments, the scale process is decomposed into two series of one-dimensional stretches.

This implies that the stretch function operates only on one-dimensional vectors and improves the efficiency. In some embodiments, the stretch function must be fast enough to operate in real-time. In some embodiments, the stretch algorithm minimizes the access to the input and output buffers, since no buffer value is accessed twice.

In some embodiments, a direct advantage of the row-by-row stretch principle is the simulation of the focus. As described before, the focus increases the image resolution at a given depth. In some embodiments, it is possible to use the stretch function to augment or reduce the resolution of different rows to provide the user with the impression of higher resolution at a given depth, while rows out of focus depth are blurred by under-sampling them and stretching them back to the image size. For example, assuming that the ultrasound has N potentiometers for the DGC function and one potentiometer for the Gain function. As explained previously, these two functions are essentially the same, and they amplify the signal reflected from the body according to the potentiometer's values. Thus, the value of the gray level of the voxel sampled at the volume buffer, denoted by V, is scaled by a scalar value Gain, to simulate the effect:

$$NewGray=MIN(Gain*V,255)$$

This effect can be applied by simply modifying the color lookup table of the display system. For the DGC effect, the N values are interpolated by a spline to the length of the image column, and stored in a lookup table DGC[ ]; so for row y:

$$NewGray=MIN(DGC[y]*V,255)$$

Combining the effect of the two functions, we get:

$$NewGray=MIN(Gain*MIN(DGC[y]*V,255),255)$$

In some embodiments, to save on computation, a 2D lookup table is used. In some embodiments, the indices to the table are the gray values and the row number. In some embodiments, each table entry contains the gray level value to be displayed for a given sample value at a given depth for a preset Gain and DGC setup. In some embodiments, this table is updated each time some potentiometer's values are modified, or whenever the image is magnified.

Data Acquisition 606

In some embodiments, the volume buffer which stores the ultrasonic data is big enough and represent a large portion of the human body to permit the bounded-free practice of a real life diagnosis. Contemporary ultrasound devices do not provide the capability of obtaining the entire volume in a single acquisition. This implies that the volume buffer has to be reconstructed from several sub-volumes obtained from different viewpoints. The registration of mono-modal datasets has been extensively investigated elsewhere in medical application where atlas data are used. However, ultrasonic datasets are far more problematic than other medical modalities, such as computed tomography (CT) or magnetic resonance imaging (MRI), since the ultrasound values are significantly noisy, blurred and have many more view-dependent variations, as mentioned above. Moreover, the data sampled from a real patient is usually deformed, as will be explained below. In some embodiments, given two volumes with a significant overlap, a spatial transformation is found which aligns and registers the two volumes into a single volume which smoothly combines the information from both. In some embodiments, the type of registration technique that can be appropriately applied is directly dependent on the type of variation between the two volumes.

Thus, to design a registration method it is necessary to know the type of variation exhibited by ultrasonic volumes.

The typical size of an ultrasound image generated by common ultrasonic devices is limited to 12-15 cm at the wide zone. The acquisition of a volume is thus reconstructed from a series of 2D slices. There are two main methods to collect the series of slices: a freehand collection and a mechanical collection.

In some embodiments, in a freehand collection the location and orientation of the slice is tracked by a six-degree-of-freedom (6DOF) device (e.g. 6DOF, Isotrack). In some embodiments, the slices are stored in the volume, and the gaps between the slices are filled by interpolations. In some embodiments, another approach used is to attach the transducer probe to a mechanical motor that sweeps the slice along some type of trajectory (e.g. fun, rotation). In particular, an example of one of these ultrasound devices is the TomTec device that offers a parallel sweep by which a series of parallel uniformly spaced slices leave no gaps. It is possible to define the image resolution which is traded off for speed. The TomTec also includes three types of motors: parallel, fun and rotational, and gating equipment for periodic movements. The parallel dense slices generated by the TomTec provide small volumes of good quality. A series of such volumes needs to be collected and assembled to form a large volume 610. The registration of two volumes requires one to detect the changes between the two images and to design a transformation that deforms them in order to remove or reduce the variations between them.

The source variations can be classified into the following three types.

Directional variations 614: These variations are due to changes in the view point. They cause a misalignment that can be simply corrected by a rigid transformation. However, as we showed above, the acquisition of the same volume from a different view point causes other effects that are not compensated for by spatial transformation. For example, shadows are cast with strong correlation with the probe viewing direction.

Volumetric variations 616: These are caused by the characteristic of the ultrasonic technology. For example, the DGC and Gain distortions and the inherent noisy and blurred ultrasound signal. These effects are difficult to model and to remove. One can attempt to reduce them by tuning the acquisition parameters.

Geometric variations 618: Geometric deformations are caused by the movements of the body during the time of acquisition. Some movements are forced by the acquisition device, since the ultrasound probe must have good contact with the body. Of course the human body is soft and not flat, and it is rather difficult to maintain contact without causing forced movements by the muscles contracting. Immersing the body in a tube of water can avoid probe contact and eliminate the muscular contractions. Another unavoidable deformation is caused by breathing and other natural behavior of the sampled body. Periodic deformation (like that of the heart) can be overcome by gating. In gating, the acquisition is synchronized with the period and the slices are acquired in the same phase of the period, using equipment similar to ECG, which monitors heart activity.

Volume Registration 608

In some embodiments, large ultrasound volumetric buffers are constructed using a series of volumes acquired by one or more ultrasound devices, for example like the TomTec or Polhemus-motion tracking 610. In some embodiments, the ultrasound device is attached to a mechanical arm with which different volumes are obtained. In some embodiments, the ultrasound device position and orientation are recorded using for example a 6DOF device with which the global misalignment can be corrected by a simple rigid transformation that maps the volumes back to a common (world coordinate) space. However, in some embodiments, the global rigid transformation is coarse, and a fine elastic deformation is needed to obtain a good registration that compensates for local shape deformations and acquisition variations. In some embodiments, the elastic deformation is local and is based on the overlapping portion of two given volumes. In some embodiments, the rigid transformation is too coarse and, even if exact, the two volumes have variations which are apparent mainly where the two volumes are in contact. In some embodiments, a direct registration method is used to automatically correct small spatial variations caused by geometric deformations. In some embodiments, the method is based on the gradient values. In some embodiments, the registration method further comprises a multi-resolution method to better deal with large misalignments. In some embodiments, the transformation is computed on a resolution pyramid and the results from the low resolution transformation are used to guide the computation of the finer levels. In some embodiments, a resolution pyramid consists of the original image and a number of copies at lower resolutions. In some embodiments, at lower resolutions adjacent pixels and local gradients represent large distances of the original image. In some embodiments, a displacement computed on a low resolution image indicates a larger displacement on the highest resolution of the original image. In some embodiments, these larger displacements may yield transformations that compensate for larger misalignments. However, in some embodiments, those are only rough transformations since they are based on coarse representations of the original images. In some embodiments, the computation of the higher levels is based on the displacements of the lower levels and refines them. In some embodiments, the multi-resolution method improves the performance of the registration in terms of the initial misalignment of the source and target images.

Exemplary Order of Displaying Ultrasound Data

In some embodiments, at any certain position of the reference element that is identified by the system, the system can display one or more ultrasound data that corresponds with the spatial orientation of the reference element.

In some embodiments, as specified above, ultrasound data comprises one or more of ultrasound videos, ultrasound volumes, and ultrasound images. In some embodiments, the instructions for displaying ultrasound data are as follows:
    a. Ultrasound videos are preferred over all others;
    b. There is no ultrasound video—display ultrasound volume instead;
    c. There is video but user is not on the right plane—display ultrasound volume instead;
    d. There is video and user is in the right plane—display video.

Figure 6B:
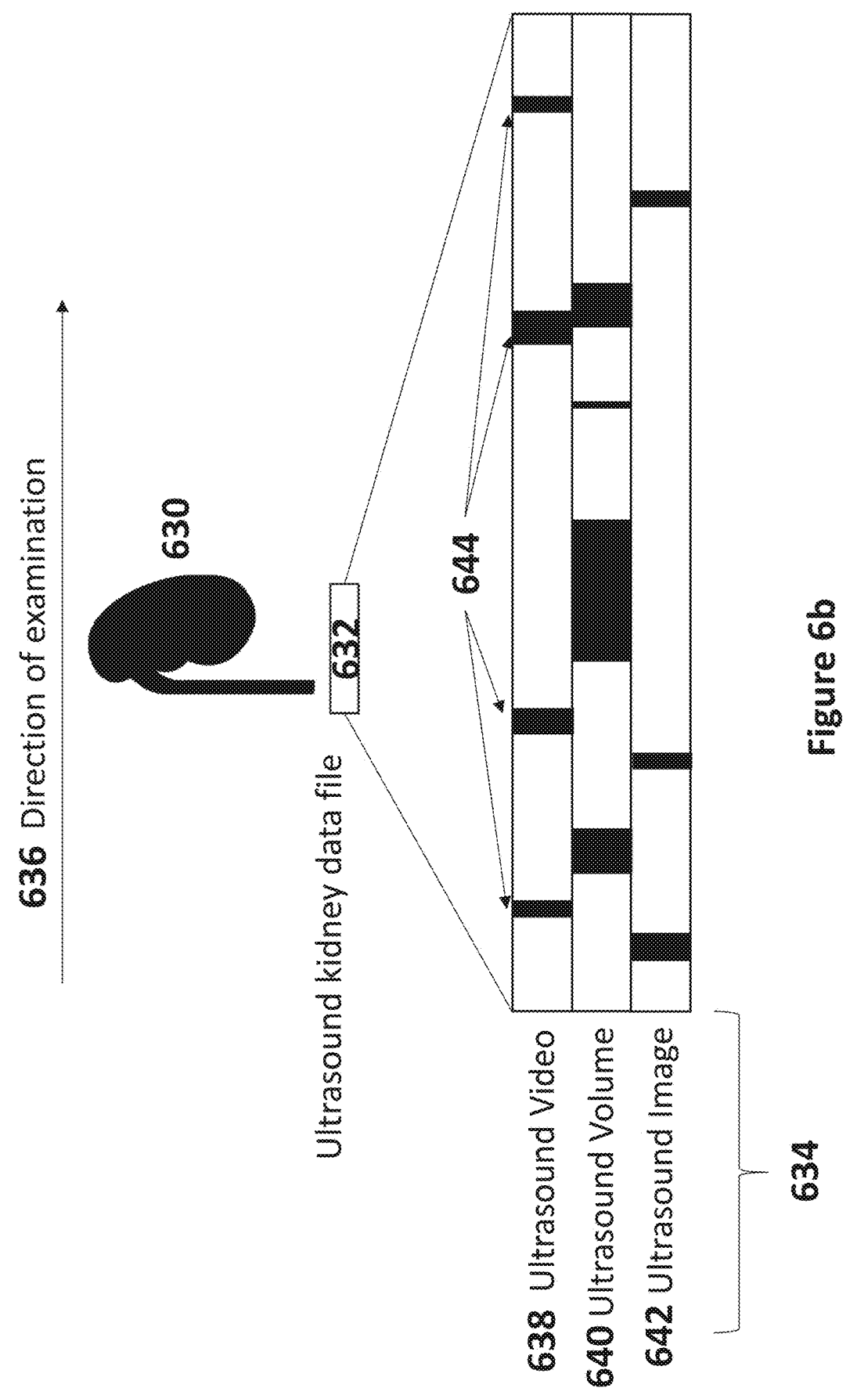
FIG. 6b is a schematic representation of an exemplary ultrasound data file comprising a plurality of sources of ultrasound data and an exemplary order of displaying ultrasound data, according to some embodiments of the invention.

Referring now to FIG. 6b, showing a schematic representation of an exemplary ultrasound data file comprising a plurality of sources of ultrasound data and an exemplary order of displaying ultrasound data, according to some embodiments of the invention. In some embodiments, the system is configured to display a plurality of ultrasound data at the same time to produce a high quality ultrasound image to be displayed. For example, the ultrasound simulation system comprises a lesson on how to perform an ultrasound examination of a kidney 630 of an adult subject. In some embodiments, the data collection module will collect all available ultrasound media for that specific area, for example, a plurality of videos, volumes and images of an examination of a kidney. In some embodiments, the system creates a dedicated media file 632 utilizing all and/or part of the ultrasound media collected 634 and are superimposed according to spatial location order 636 of examination, for example, a kidney when examined from left to right, as shown in FIG. 6b. To facilitate the explanations, the ultrasound kidney data file 632 is represented as a video track having a beginning and an end, where the beginning is on the left side of the kidney and the end is on the right side of the kidney that is being examined (according to the direction of the examination 636). In some embodiments, the ultrasound kidney data file 632 is composed of superimposed ultrasound video files 638, ultrasound volume files 640 and ultrasound image files 642. In some embodiments, superimposing is dictated of what is shown in the ultrasound file, for example, meaning the same location in the kidney shown by all ultrasound data files.

In some embodiments, as shown in FIG. 6b, for example the ultrasound video file 638 is missing certain zones or comprises zones of lower quality, as identified by black squares 644 in the video track. In some embodiments, on those locations where there is no video available, the system will show the next available ultrasound data file for that location, optionally according to a predetermined quality order, as disclosed above.

In some embodiments, the software is configured to merge between the different sources of ultrasound data to provide a high quality ultrasound image to be displayed.

Exemplary Use of Doppler/Color Doppler

In some embodiments, the system further comprises a library of Doppler/Color Doppler images/videos, which are displayed concomitantly to the ultrasound image. The term 'Doppler' refers hereinafter to any kind of Doppler image/ video, whether is a graph or color or a combination thereof, the term 'Doppler' will be used for commodity but it should be understood that all types of Doppler assays are included therein. In some embodiments, the Doppler data is displayed over the 2D ultrasound image/video. In some embodiments, the Doppler data is displayed over the ultrasound volume. In some embodiments, on top of the three-dimensional volume, a vector layer, of tubes or other cavities, will be combined with a flow with properties controlled by the system, for example: flow direction, frequency, pulse, amplitude of the wave that is equal to the contraction of the systolic wave S, amplitude height of the end diastolic wave, and other. In some embodiments, the vector information is expressed and displayed in relation to the given section in one or more ways. For example, the appearance of a color in a hue representing the flow velocity and the flow direction. In some embodiments, when bringing the marker of 'sample volume' in the color, the trainee will be shown a flow wave image calculated according to the wave characterization as was previously set in the system.

Exemplary Principle of the System

Figure 7A:
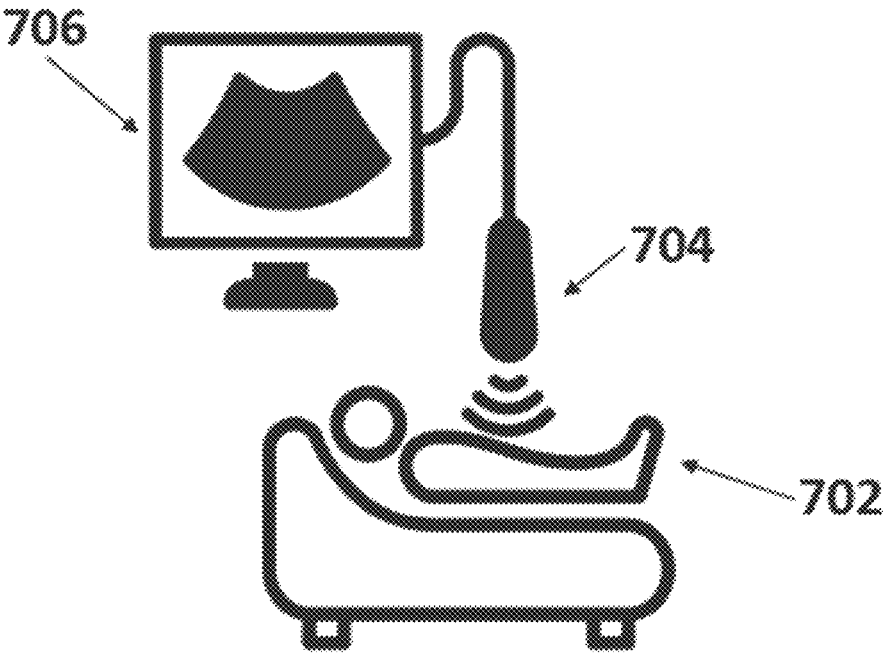
FIGS. 7a-b are schematic illustrations showing an exemplary principal of the system, according to some embodiments of the invention.
Figure 7B:
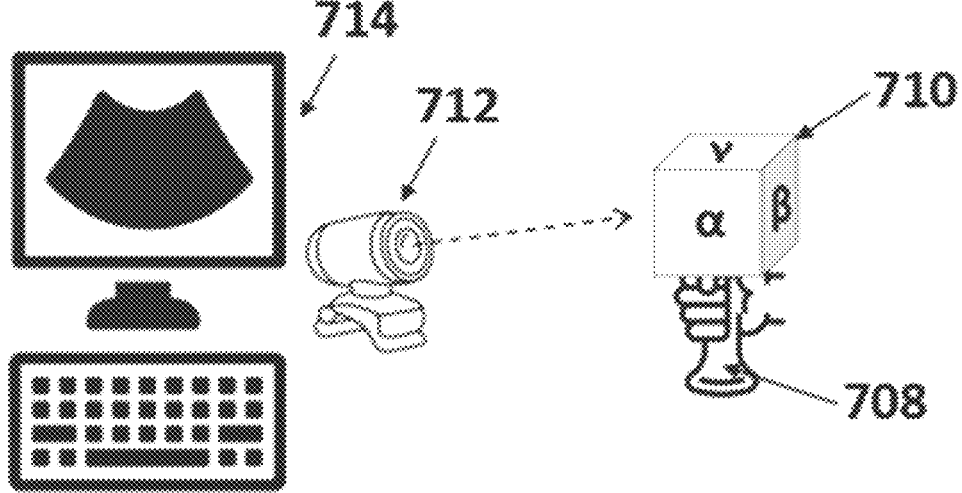

In some embodiments, an exemplary principal of the system is receiving images from a camera, automatically identifying a reference element comprising one or more reference markings, automatically tracking spatial movements of the reference element, correlate the tracked spatial movements of the reference element with recorded spatial movements of ultrasound transducers, which are associated with specific 2D ultrasound images and automatically showing ultrasound images/videos/volumes to the user, according to the correlations, which match what a user would see if they would have been doing an actual ultrasound examination. Referring to FIGS. 7a-b, showing a schematic illustration showing an exemplary principal of the system, according to some embodiments of the invention. FIG. 7a shows a schematic illustration of a patient 702 being submitted to ultrasound examinations 704 using a transducer 704 where the images seeing during the examinations are shown in the ultrasound's screen 706. As explained above, the user moves the transducer 704 over the patient 702, and that movement comprises certain tridimensional spatial movement characteristics, which are recorded (as explained above), correlated and associated with registered 2D ultrasound slice images (which can then show one or more of ultrasound images/videos/volumes).

In some embodiments, optionally, the procedure parameters and information are saved in a database on a server, as explained above.

FIG. 7b shows a schematic illustration of an exemplary principle of the system, according to some embodiments of the invention. In some embodiments, a user holds an object 708 (for example a stick or a handle) comprising a marker element 710. In some embodiments, the software tracks the spatial movements of the marker element 710, by means of the spatial location reference marker module 406 in the processing module 404, using the information received by a camera 712 (430 in FIG. 4a), and when the spatial movements tracked by the software match the recorded spatial movements of a transducer saved in the database, the display module 412 shows the ultrasound data (image/video/volume) in the computer's screen 714 (432 in FIG. 4a).

In some embodiments, the system is also configured to display expected tridimensional movements of a transducer and/or a reference element using ultrasound input.

In some embodiments, the system is configured to record simulation sessions comprising the recording of one or more type of (for example) the case simulated, identified movements of said tridimensional reference element, time to finish simulation, time to reach the requested area and images chosen to keep during simulation.

Exemplary Graphical User Interface (GUI)

In some embodiments, the system comprises a graphical unit interface (GUI) configured to be displayed in the electronic device by the display module. Referring now to FIG. 8a showing an exemplary GUI, according to some embodiments of the invention.

In some embodiments, on the GUI there can be displayed one or more of the following:

Name of the device/system and logo 802, name of the school and/or organization the instructor belongs to, data and time, topic of the simulation 804, specific patient examined during the simulation/examination comprising name of patient, patient ID, age, patient data (for example one or more of LMP, Gravida, Ectopic, Para, AB, no. of fetuses, GA, general description, reference number, reason for examination, comments and diagnosis), Scans 806 (For example one or more of GYN, OB early and OB 2-3), measurements (For example one or more of review, parameters, 2D measurements and graphs), B-mode, M-mode, Doppler, comments, body marks, findings, type of probes, settings 808 (for example one or more of TGC, Freq, Depth, Gain, Focus), Print, Freeze, Store, SCAN (for example one or more of Shock, eFAST, Lung, Abdomen, OB/GYN, MSK, Nerve and Rheumatology), Start Exam, End Exam, Parameters (for example one or more of PI, RI.TAMAX and HR).

In some embodiments, on the GUI, according to the topic of the simulation and the syllabus, a tridimensional model of the organ/patient/fetus 810 will be displayed on the GUI, as shown for example in FIGS. 8b-c. In some embodiments, on the tridimensional model of the organ/patient/fetus there will be zones 812a-b marked which corresponds with the ultrasound data located in the ultrasound library database, as shown for example in FIG. 8c.

Exemplary 'HELP' Feature

In some embodiments, the system comprises a 'help' feature, which is basically a commend that allows the trainee to request assistance during the training session. In some embodiments, assistance is provided in a plurality of ways, for example, by pressing the 'help' button, the system displays a virtual transducer on the screen at a specific 'orientation in space' and the trainee is requested to position his transducer at the same orientation. In some embodiments, from this point, the trainee can continue the training exercise. In some embodiments, another example, by pressing the 'help' button, the system displays what the camera of the trainer is showing (when the trainer is also performing the exercise in parallel with the trainees for training purposes) so the trainer can perform and show the correct movements to the trainee that requires assistance. In some embodiments, the trainee then can continue with the exercise. In some embodiments, a potential advantage of this feature is that assistance can also be done remotely, when the trainee and the trainer are not located in the same location.

Exemplary Uses of the System

In some embodiments, the system can be used for example for one or more of training purposes, for review of ultrasound data by professionals, for review of ultrasound by the patients themselves and monitor ultrasound examinations in real time.

Exemplary Training

In some embodiments, users learning how to perform ultrasound examinations use the system to learn and/or improve how to move the transducer to achieve the desired result, optionally at the shortest time possible. A potential advantage of the system is that it allows to train an infinite number of users without the need of expensive purpose-built classrooms or manikins.

In some embodiments, the training system comprises a plurality of "training session" generated from one or more "unified collection of ultrasound information" files. In some embodiments, the training includes tasks, for example, reaching a certain section, making measurements, inserting signs, correct operation of buttons and answering questions. In some embodiments, the trainer defines the tasks.

In some embodiments, the trainer can combine several "unified collection of ultrasound information" files into a "unified training information" file, where optionally, the volumes are located in a known space and are spatially integrated according to their coordinate system. In some embodiments, the trainer can move the positions of each of the united files.

In some embodiments, the training system comprises an automatic scoring of defined tasks. In some embodiments, the trainer can define the score on the basis of various parameters, for example, the trainee's seniority, experience, field of practice, length of time to accomplish the task.

In some embodiments, the training system is configured to analyze the orientation in the 3D-space by assessing the position of the transducer in the real world using a camera over time. For example, there are provided two sections, one defined as the starting point and the other as the end point (defined by the trainer for example), the "route" performed by the trainee between the starting point and the end point will be evaluated using a plurality of parameters, for example, time, movement, total movements, time distance from the "correct" route (inserted a priori by the trainer). In some embodiments, the use of parameters allows automatic analysis of the quality of performance of the trainee.

In some embodiments, a plurality of trainees can access the same training session simultaneously.

In some embodiments, as mentioned elsewhere in this document, the system comprises a database with one or more libraries of three-dimensional models, for example of internal organs (i.e. the brain and heart) and anatomical bodies with the external appearance of the surface (i.e. the abdomen, chest, waist and limb).

In some embodiments, an additional reference element can be optionally placed on the trainee's work surface, which will be used as reference to place the virtual body on the computer screen.

In some embodiments, the system comprises a dedicated control interface, associated with the display module, comprising the same and/or more of control "buttons" expected to be found in a real ultrasound machine. In some embodiments, the dedicated control interface is a virtual control interface, which is shown in the screen. In some embodiments, the dedicated control interface is an additional peripheral hardware that is connected to the computer in the same way a keyboard and/or a mouse connects to a computer. In some embodiments, the user practices on controlling and/or modifying parameters related to ultrasound examinations while moving the reference element. In some embodiments, the system is configured to perform tracking of multiple targets (i.e. cubes) that can represent, for example, one or more of a transducer, needle, camera, or any other surgical tool. In some embodiments, ultrasound machine parameters are one or more of Frequency, Gain, Sensitivity, Depth, Modes of scanning, Zoom, Tissue Harmonic Imaging, Freeze and Caliper/Calculations.

In some embodiments, the training system comprises a virtual button panel (in addition to the ultrasound window), which allows to adapt the functionality of existing panels of real ultrasound systems into the training system.

In some embodiments, the training system allows a plurality of different types of training sessions, for example, trainee training alone and/or trainee receiving instruction from the trainer in real time.

In some embodiments, the training system display comprises a display of the degree of progress and quality of performance of the trainee. In some embodiments, during and/or after an individual training session, the trainee's performance analysis is used to adjust the follow-up training session according to the trainee's performance—thus providing an adaptable personalized training for each of the trainees.

In some embodiments, performance analysis is performed using one or more parameters, for example:

1. Trainee's capability to position the transducer in space in order to provide and display the required image requested by the training program;
2. Trainee's movements of transducer performed from the start point to the end point, for example, continuity of movement, velocity of movements, steadiness of movement, whether the trainee does zigzag movements in general and/or towards the required position by the training program, whether the final tuning at the required location is done fast or slow, and in general the characterization of the fine tuning performed by the trainee.
3. Trainee's capability to position markers in the ultrasound displayed image, perform measurements, identification of what is shown in the ultrasound displayed image.

4. Trainee's capability to actuate the controls of the ultrasound device (mock controls of the ultrasound device displayed in the screen).
5. Trainee's capability to respond to questions related to diseases/pathologies of what is displayed in the ultrasound displayed image.

In some embodiments, the analysis is performed by an AI software, comprising instructions to learn from each trainee on how to evaluate performance and therefore optionally provide personalized recommendations to each trainee.

In some embodiments, the system comprises a report module configured to generate trainee performance reports, comprising for example: duration of session, types of training, trainee performance, and level of competence according to different categories.

In some embodiments, the training system provides a training certificate according to criteria. In some embodiments, a potential advantage of the system, is that it allows a standardization for ultrasound training, which can be used around the world. In some embodiments, the system is used as a worldwide recognized standardized ultrasound training system.

In some embodiments, the training software comprises one or more modules configured to record the performance of the users during the training sessions. In some embodiments, recorded data is used to monitor the improvement of the user over a period of time and to monitor specific areas in which the user needs to improve.

In some embodiments, the software comprises a machine learning algorithm configured to monitor each user's performance. In some embodiments, each user's performance is compared to one or more of: a predetermined standard, a predetermined gold-standard and to other users in the same group of users, for example, other students in the same group. In some embodiments, the machine learning algorithm utilizes the performance to provide recommendations of how to proceed with the training.

In some embodiments, the training software comprises a library of cases that a user can access and practice. In some embodiments, the library of cases is saved and/or access the ultrasound library database 410.

In some embodiments, the training software combines didactic instruction with exploratory learning via trial and error. A potential advantage of this structure is that specific lesson plans can be updated periodically with new material, allowing for the creation of a large encyclopedia of lessons using the same scanned data several times.

Exemplary Use of the System as a Training Tool for Processing Ultrasound Information In some embodiments, the system is used to teach trainees how to process ultrasound data. For example, how to process 2D ultrasound data into 3D ultrasound data, how to process that generated 3D ultrasound data, presenting perpendicular planes of the collection plane, thus allowing the presentation of surface planes such as fetus face, etc.

Exemplary Use of Alternative Information as Additions to the System

In some embodiments, the system comprises one or more additional information that can be displayed to the trainee during a training session. For example, CT and/or MRI and/or CT-MRI images/videos of the relevant area where the ultrasound images are being taken can be displayed in parallel to complement the training and provide another layer (for example anatomy teachings) of teaching to the ultrasound training program.

US 12,599,364 B2

35
36

Exemplary On-Line Training

In some embodiments, any of the training information, training session, training programs described herein can be performed remotely in an on-line training session. In some embodiments, the training system is configured to use any of the known on-line communication platforms (i.e. Zoom©, Microsoft Teams, Nextiva, Slack, Guru, Confluence, Zendesk, Zoho Desk, Hiver, atc) to perform on-line training sessions.

Exemplary Training Lesson

An exemplary training lesson can be as following: The instructor explains a medical case and provides to the students the scope of the lesson. The students will receive instructions of what is required to find in the ultrasound examination. The students begins the virtual examination using the system and the system begins monitoring the actions and/or the performance of the students during the ultrasound examination. Then the students are required to provide data related to the ultrasound examination that they had performed by means, for example, of a questioner.

Exemplary Use of the System by Medical Professionals

In some embodiments, medical professionals can use the system to review ultrasound examinations performed on patients. In some embodiments, original ultrasound files of patients are inserted in the system, and after analysis and processing, the file is augmented with the 3D positional data of the transducer, as explained above. Then, the medical professional can review the augmented file from his computer using a reference element and look exactly for what he is interested in, without the need to review the whole ultrasound recording.

In some embodiments, medical professionals can use the system to review ultrasound examinations performed on patients to provide second opinion to the users and/or other medical professionals.

Exemplary Use of the System by Patients

In some embodiments, the patients can use the system to review ultrasound examinations performed on themselves. For example, a patient had an ultrasound examination of his kidneys. Later at home, the patient can review the examination to see what was diagnosed and/or mentioned by the medical practitioner.

Exemplary Use of the System for Performance Monitoring of Examinations

In some embodiments, the system can be used to monitor that all that is required for a certain examination was performed by the medical professional. For example, a woman is required to have an ultrasound examination to search for fetal abnormalities. The medical professional will have a reference element coupled to the transducer and a parallel system comprising the system of the invention, in addition to the ultrasound machine. The system of the invention will monitor the movements performed by the medical professional and, knowing the scope of the ultrasound examination, the system will warn the professional if not all required acquisitions of ultrasound data were performed, and which ones are still needed.

Exemplary Use of the System for Liability Purposes

Similar to what was described above regarding performance monitoring of examinations, the system is used for liability purposes. The system is used to monitor the actions of the medical professional to assure that all what was needed to do during an examination was performed and was performed correctly, in comparison to a gold-standard for examinations of the same type. The recording can be used later to assess the liability of the medical professional if needed.

Exemplary Use of the System for Monitoring of Quality Data During Examinations

In some embodiments, the system can be used for monitoring quality of data acquired during an ultrasound examination. For example, the reference element is used during the ultrasound examination to provide relative data between the picture data received and the reference element itself. For example, if the received picture data does not change over a specified period of time it means that the object observed is not moving, which is a positive feedback information when assessing organs for example. If the received picture data does change over a specified period of time it means that the object observed is moving, which is a positive feedback information when assessing fetuses, since a fetus that does not move could indicate a problem with the fetus.

Exemplary Use of the System for Generating 3D Files for Public Publications

In some embodiments, the 3D image generated using the system and/or the robotic scanner is accessed by using a dedicated link and/or a QR (previously generated). In some embodiments, for example, an author can include a dedicated link and/or a QR to an article to allow readers to access the ultrasound 3D images related to the article.

Exemplary Use of the System for Other Fields

In some embodiments, the system can be adapted to be used as a simulation system in other fields and/or scopes, for example Otoscopes, Ophthalmoscopy Exams, Heart auscultations, Lung auscultations, insertion of a needle or trocar into an abdominal cavity.

Figure 9A:
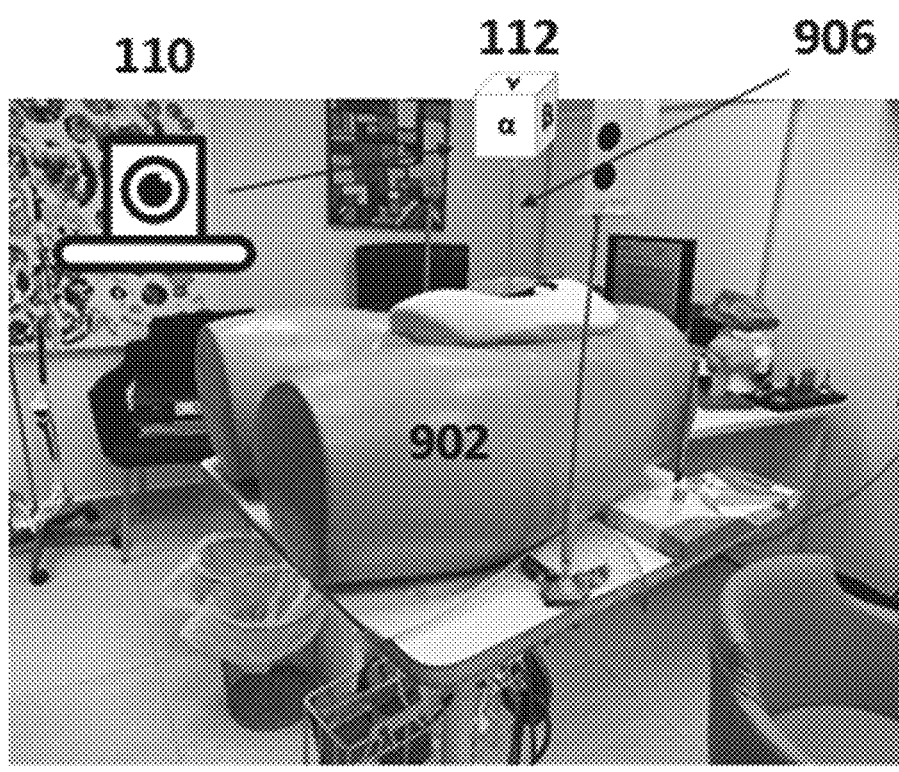
FIGS. 9a-b are schematic representations of an exemplary use of the system for the simulation of the insertion of a needle/trocar, according to some embodiments of the invention.
Figure 9B:
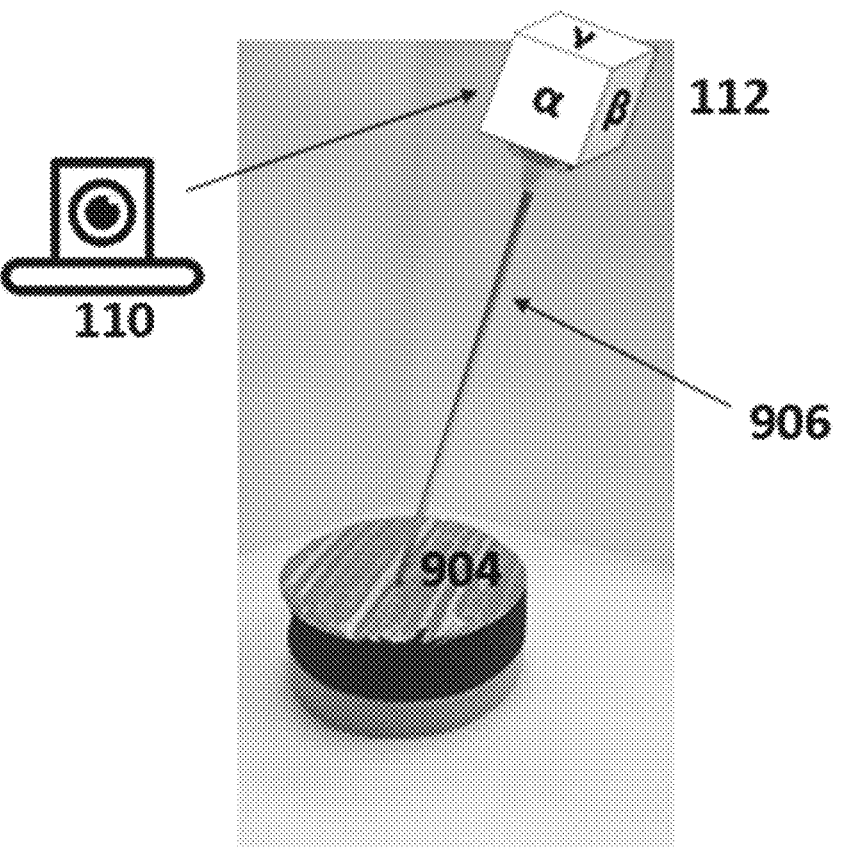

Referring now to FIGS. 9a-b showing an exemplary use of the system for the simulation of the insertion of a needle/trocar, according to some embodiments of the invention. In some embodiments, instead of providing information about the spatial movements of a transducer, the system is configured to provide and/or monitor movements of a reference element 112 as movements of a trocar/needle 906. In some embodiments, optionally, a mannequin 902 (shown in FIG. 9a) and/or a demo-tissue element 904 (shown in FIG. 9b) are used to monitor and evaluate the movements performed by a user during the insertion of a trocar/needle. In some embodiments, a reference element is positioned on the trocar/needle, and a camera 110 monitors the movement of the reference element to assess the performance of the user during the insertion of the trocar/needle. In some embodiments, demo-tissue elements are used to mimic the actual tissues that will be encountered during the actual use of the trocar/needle.

Figure 10:
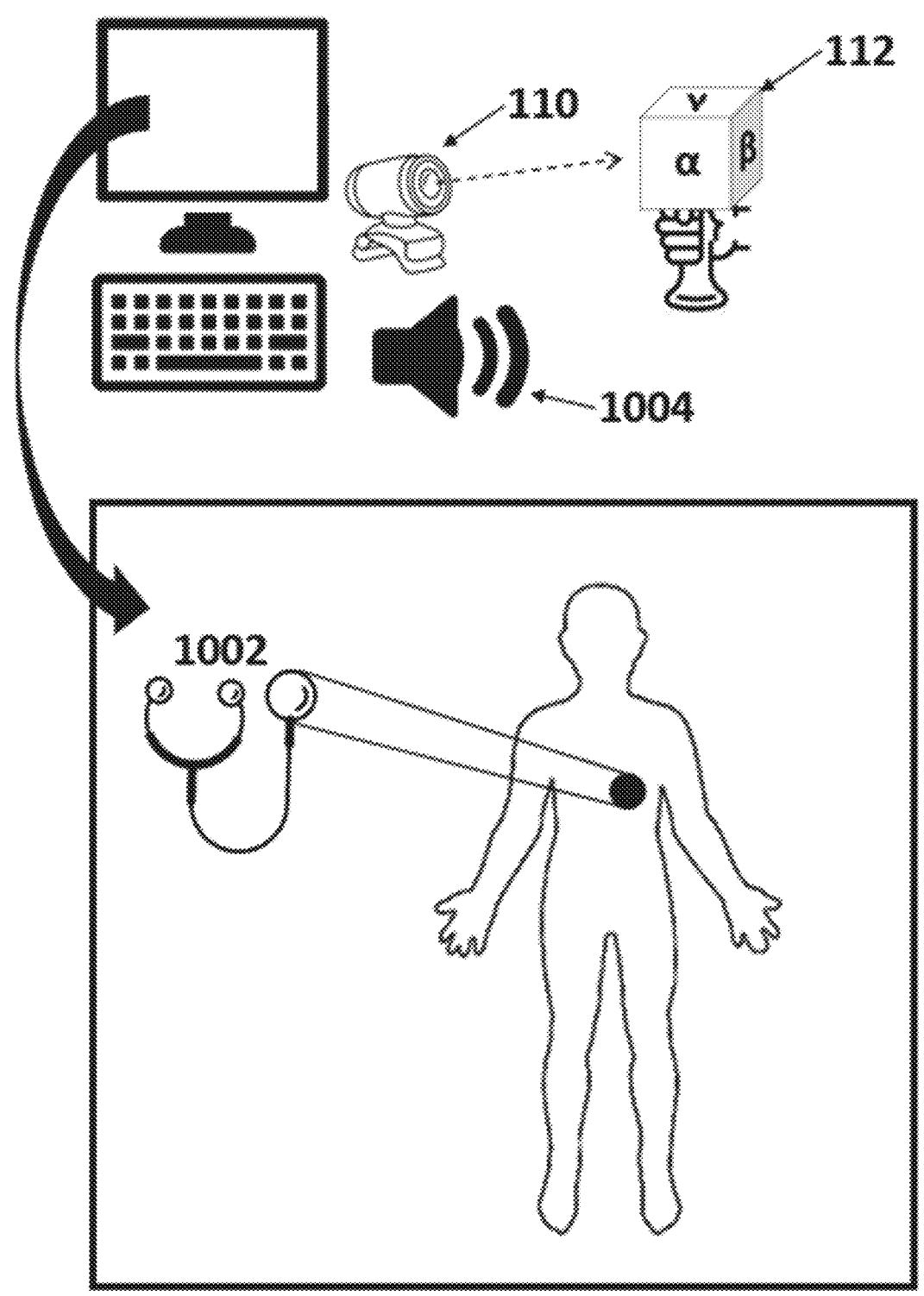
FIG. 10 is a schematic representation of an exemplary use of the system for the simulation of the use of a stethoscope, according to some embodiments of the invention.

Referring now to FIG. 10, showing an exemplary use of the system for the simulation of the use of a stethoscope, according to some embodiments of the invention. In some embodiments, instead of providing information about the spatial movements of a transducer, the system is configured to provide and/or monitor movements of a reference element 112 as movements of a stethoscope 1002. In some embodiments, optionally, a mannequin (not shown) are used to monitor and evaluate the movements performed by a user during the use of the stethoscope. In some embodiments, a reference element 112 is moved, and a camera 110 monitors the movement of the reference element 112 to assess the position of the stethoscope 1002 during an examination. In some embodiments, utilizing dedicated speakers 1004 the system sounds what a user would when performing an examination. In some embodiments, on the screen, the system displays the virtual location of the stethoscope on the body, while sounding for example, the sound of heart beats.

Figure 11:
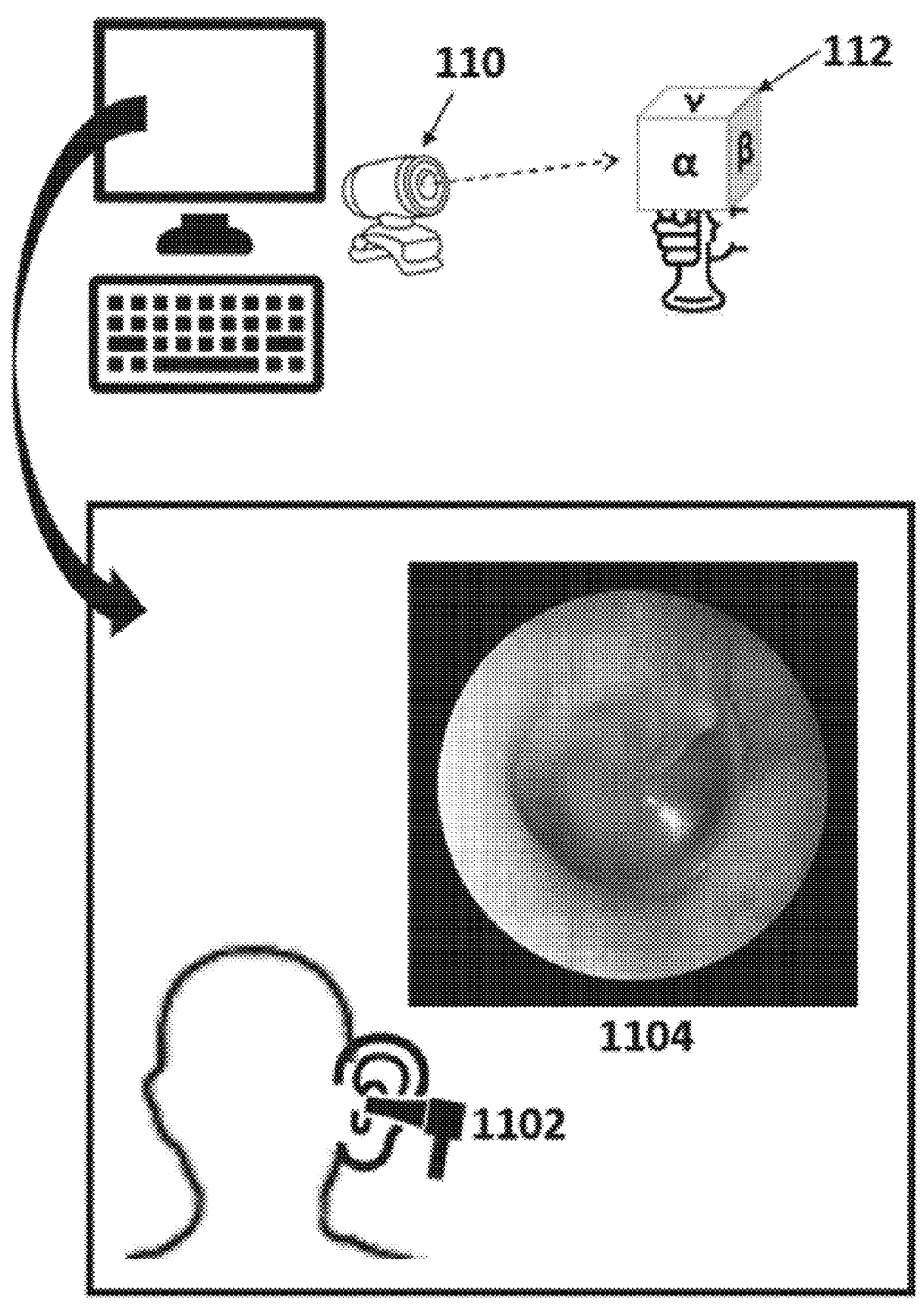
FIG. 11 is a schematic representation of an exemplary use of the system for the simulation of the use of an otoscope, according to some embodiments of the invention.

Referring now to FIG. 11, showing an exemplary use of the system for the simulation of the use of an otoscope, according to some embodiments of the invention. In some embodiments, instead of providing information about the spatial movements of a transducer, the system is configured to provide and/or monitor movements of a reference element 112 as movements of an otoscope 1102. In some embodiments, optionally, a mannequin (not shown) are used to monitor and evaluate the movements performed by a user during the use of the otoscope. In some embodiments, a reference element 112 is moved, and a camera 110 monitors the movement of the reference element 112 to assess the position of the otoscope 1102 during an examination. In some embodiments, on the screen, the system displays the virtual location of the otoscope on the body, while displaying 1104 for example, what is seen at that location by the otoscope.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for simulating an ultrasound, comprising:
   a. providing an ultrasound library database of ultrasound data and corresponding first spatial data of a transducer during which said ultrasound data was acquired relative to an orientation of a target;
   b. digitally imaging a physical tridimensional reference element being held by a user and being identified as an ultrasound probe being used during a simulated ultrasound scan;
   c. determining from said imaging a second spatial data of said physical tridimensional reference element relative to a virtual location-identifying orientation;
   d. comparing said second spatial data of said physical tridimensional reference element with said first spatial data of a transducer; and
   e. displaying said ultrasound data when said second spatial data is the same as said first spatial data and said orientation of a patient is the same as said virtual location-identifying orientation.

2. The method according to claim 1, wherein said providing an ultrasound library database of a plurality of ultrasound data comprises providing one or more of ultrasound images, ultrasound videos and ultrasound volumes.

3. The method according to claim 1, wherein said displaying said ultrasound data comprises displaying said ultrasound data according to a predetermined order; and wherein said predetermined order is according to one or more of:
   a. a quality of said ultrasound data; and
   b. a predetermined order which is ultrasound video, ultrasound image and ultrasound volume.

4. The method according to claim 2, wherein said displaying said ultrasound data comprises displaying a merged image from said one or more of ultrasound images, ultrasound videos and ultrasound volumes.

5. The method according to claim 1, wherein said first and said second spatial data comprises one or more movements and directions selected from the group consisting of up, down, forward, backwards, right, left roll, yaw, pitch and any combination thereof.

6. The method according to claim 1, wherein said virtual location-identifying orientation is a virtual orientation of one or more of a virtual patient and a virtual target.

7. The method according to claim 1, wherein said physical tridimensional reference element comprises at least one reference markings.

8. The method according to claim 7, wherein said determining said second spatial data of said tridimensional reference element comprises one or more of:

a. identifying said at least one reference markings;

b. identifying movements of said tridimensional reference element according to said identification; and c. correlating said identified movements with said virtual location-identifying orientation.

9. An ultrasound simulation system, comprising:

a. a physical tridimensional reference element configured to be held by a user;

b. a software configured for:

i. digitally imaging said physical tridimensional reference element being held by a user and being identified as an ultrasound probe being used during a simulated ultrasound scan;

ii. determining from said imaging a second spatial data of said physical tridimensional reference element relative to a virtual location-identifying orientation;

iii. comparing said second spatial data of said physical tridimensional reference element with said first spatial data of a transducer; and iv. displaying said ultrasound data when said second spatial data is the same as said first spatial data and said orientation of a patient is the same as said virtual location-identifying orientation.

10. The ultrasound simulation system according to claim 9, wherein said physical tridimensional reference element comprises a hexagonal prism form.

11. The ultrasound simulation system according to claim 9, wherein said physical tridimensional reference element comprises at least one reference markings.

12. The ultrasound simulation system according to claim 9, wherein said image is identified from data received from a camera.

13. The ultrasound simulation system according to claim 11, wherein said ultrasound data is one or more of ultrasound images, ultrasound videos and ultrasound volumes;

wherein said one or more of ultrasound images, ultrasound videos and ultrasound volumes are cataloged in an ultrasound library using a spatial correlation between each other according to what is shown in them; and wherein said displaying said ultrasound data comprises displaying a merged image from said one or more of ultrasound images, ultrasound videos and ultrasound volumes.

14. The ultrasound simulation system according to claim 9, wherein an ultrasound data provided due to said request is a selected algorithmic ultrasound data.

15. The ultrasound simulation system according to claim 9, wherein said displaying said ultrasound data comprises displaying said ultrasound data according to a predetermined order; and wherein said predetermined order is according to one or more of:

a. a quality of said ultrasound data; and b. a predetermined order which is ultrasound video, ultrasound image and ultrasound volume.

16. The ultrasound simulation system according to claim 9, wherein said software is further configured for identifying spatial data of said physical tridimensional reference element comprising one or more movements selected from the group consisting of up, down, forward, backwards, right, left roll, yaw, pitch and any combination thereof.

17. The ultrasound simulation system according to claim 11, wherein said identifying comprises identifying a virtual location-identifying orientation which is a virtual orientation of one or more of a virtual patient and a virtual target;

wherein said identifying an image of said physical tridimensional reference element comprises one or more of:

a. identifying said at least one reference markings;

b. identifying movements of said tridimensional reference element according to said identification; and c. correlating said identified movements with said virtual location-identifying orientation; and wherein said system records said identified movements of said tridimensional reference element.

18. The ultrasound simulation system according to claim 9, wherein said physical tridimensional reference element comprises at least one selected from the group consisting of a light, a vibration mechanism and a speaker.

19. The ultrasound simulation system according to claim 9, wherein said system records all information related to a performed simulation by a user comprising one or more of type of case simulated, identified movements of said tridimensional reference element, time to finish simulation, time to reach the requested area and images chosen to keep during simulation.

20. The ultrasound simulation system according to claim 9, wherein said system further comprises an augmented reality (AR) activator for activating an augmented reality image to be shown to a user while using said ultrasound simulation system and wherein said augmented reality image is displayed on one or more of a display, a display on top of a real world image capture by said camera, a smart electronic device and a display on a smart glasses.

21. The method according to claim 1, wherein said displaying comprises displaying said user while performing said simulated ultrasound scan.

22. The method according to claim 1, wherein said method is a method for ultrasound training simulation that utilizes off-line pre-processed real-ultrasound images.

23. The ultrasound simulation system according to claim 9, wherein said displaying comprises displaying said user while performing said simulated ultrasound scan.

24. The ultrasound simulation system according to claim 9, wherein said ultrasound simulation system is used for ultrasound training simulation that utilizes off-line pre-processed real-ultrasound images.

\* \* \* \* \*